US009725491B2

(12) United States Patent
Sahillioglu et al.

(10) Patent No.: US 9,725,491 B2
(45) Date of Patent: Aug. 8, 2017

(54) METHOD FOR ANTIGEN DELIVERY

(71) Applicant: BOGAZICI UNIVERSITESI, Istanbul (TR)

(72) Inventors: Ali Can Sahillioglu, Istanbul (TR); Nesrin Ozoren, Istanbul (TR)

(73) Assignee: Bogazici Universitesi, Istanbul (TR)

( * ) Notice: Subject to any disclaimer, the term of this patent is extended or adjusted under 35 U.S.C. 154(b) by 229 days.

(21) Appl. No.: 14/396,632

(22) PCT Filed: Apr. 18, 2013

(86) PCT No.: PCT/IB2013/053079
§ 371 (c)(1),
(2) Date: Apr. 8, 2015

(87) PCT Pub. No.: WO2013/160807
PCT Pub. Date: Oct. 31, 2013

(65) Prior Publication Data

US 2015/0141627 A1 May 21, 2015

(30) Foreign Application Priority Data

Apr. 24, 2012 (TR) ................................ 2012 04773

(51) Int. Cl.
*C07K 14/00* (2006.01)
*C07K 14/47* (2006.01)
*A61K 47/48* (2006.01)
*C07K 14/50* (2006.01)

(52) U.S. Cl.
CPC ...... *C07K 14/4747* (2013.01); *A61K 47/4833* (2013.01); *C07K 14/503* (2013.01); *C07K 2319/50* (2013.01); *C07K 2319/70* (2013.01)

(58) Field of Classification Search
CPC ............................................ C12Y 304/22055
See application file for complete search history.

(56) References Cited

U.S. PATENT DOCUMENTS 6,911,306 B1 6/2005 Vertino
2009/0104200 A1 4/2009 Keane et al.

FOREIGN PATENT DOCUMENTS

DE WO 2006066917 A2 * 6/2006 ....... G01N 33/57419
WO WO-02/44354 A2 6/2002
WO WO-2009/014863 A2 1/2009
WO WO-2010/036918 A2 4/2010

OTHER PUBLICATIONS

Fernandes-Alnemri et al. 2007; The pyroptosomes: a supramolecular assembly of ASC dimers mediating inflammatory cell death via caspase-1 activation. Cell Death Differ. 14(9): 1590-1604.*
Ellebedy et al. 2011; Inflammasome-independent role of apoptosis-associated speck-like protein containing CARD (ASC) in the adjuvant effect of MF59. PNAS 108(7): 2927-2932.*
Han et al., 2007. Solubilization of aggregation-prone heterologous proteins by covalent fusion of stress-responsive proteins by covalent fusion of stress-responsive *Escherichia coli* protein, SlyD. Protein Engineering, Design, & Selection. 20(11):543-549.*
Mueller et al., "Antibody Conjugates with Morpholinodoxorubicin and Acid-cleavable Linkers," Bioconjug Chem. 1(5):325-30 (1990).
Maltman et al., "Enzyme-cleavable linkers for peptide and glycopeptide synthesis," Org Biomol Chem. 3(14):2505-7 (2005).
Franchi et al., "The inflammasome: a caspase-1-activation platform that regulates immune responses and disease pathogenesis," Nat Immunol. 10(3):241-7(15 pages) (2009).
International Search Report and Written Opinion for International Patent Application No. PCT/IB2013/053079, dated Sep. 20, 2013 (9 pages).
International Preliminary Report on Patentability for International Patent Application No. PCT/IB2013/053079, dated Oct. 28, 2014 (5 pages).
Examination Report prepared by the Swedish Patent Office for Turkish Patent Application No. 2012/04773, dated Sep. 17, 2014 (4 pages).
Search Report prepared by the Swedish Patent Office for Turkish Patent Application No. 2012/04773, dated Oct. 31, 2012 (7 pages).
Grant Decision issued by the Turkish Patent Institute for Turkish Patent Application No. 2012/04773, dated Sep. 19, 2014 (1 page).

* cited by examiner

*Primary Examiner* — Karen Cochrane Carlson
(74) *Attorney, Agent, or Firm* — Clark & Elbing LLP; Susan M. Michaud

(57) ABSTRACT

The present invention provides methods for antigen and/or bioactive molecule delivery to antigen presenting cells utilizing ASC specks as vehicles; 1) the ASC speck composition is made of ASC protein(s) and the antigen and/or bioactive molecule(s) purified from cells as a compact micro-spherical structure; 2) purified micro-spherical ASC speck delivery vehicles are stable at 37° C. for more than 30 days; and 3) antigen and/or bioactive molecules carried by ASC specks can be efficiently phagocytosed by antigen presenting cells and their degradation in the lysosome allows antigen processing and presentation.

24 Claims, 8 Drawing Sheets

SEQUENCE LISTING

```
<160> NUMBER OF SEQ ID NOS: 15

<210> SEQ ID NO 1
<211> LENGTH: 195
<212> TYPE: PRT
<213> ORGANISM: Homo sapiens

<400> SEQUENCE: 1

Met Gly Arg Ala Arg Asp Ala Ile Leu Asp Ala Leu Glu Asn Leu Thr
1               5                   10                  15

Ala Glu Glu Leu Lys Lys Phe Lys Leu Lys Leu Leu Ser Val Pro Leu
            20                  25                  30

Arg Glu Gly Tyr Gly Arg Ile Pro Arg Gly Ala Leu Leu Ser Met Asp
        35                  40                  45

Ala Leu Asp Leu Thr Asp Lys Leu Val Ser Phe Tyr Leu Glu Thr Tyr
    50                  55                  60

Gly Ala Glu Leu Thr Ala Asn Val Leu Arg Asp Met Gly Leu Gln Glu
65                  70                  75                  80

Met Ala Gly Gln Leu Gln Ala Ala Thr His Gln Gly Ser Gly Ala Ala
                85                  90                  95

Pro Ala Gly Ile Gln Ala Pro Pro Gln Ser Ala Ala Lys Pro Gly Leu
            100                 105                 110

His Phe Ile Asp Gln His Arg Ala Ala Leu Ile Ala Arg Val Thr Asn
        115                 120                 125

Val Glu Trp Leu Leu Asp Ala Leu Tyr Gly Lys Val Leu Thr Asp Glu
    130                 135                 140

Gln Tyr Gln Ala Val Arg Ala Glu Pro Thr Asn Pro Ser Lys Met Arg
145                 150                 155                 160

Lys Leu Phe Ser Phe Thr Pro Ala Trp Asn Trp Thr Cys Lys Asp Leu
                165                 170                 175

Leu Leu Gln Ala Leu Arg Glu Ser Gln Ser Tyr Leu Val Glu Asp Leu
            180                 185                 190

Glu Arg Ser
        195


<210> SEQ ID NO 2
<211> LENGTH: 239
<212> TYPE: PRT
<213> ORGANISM: Aequorea victoria
```

<400> SEQUENCE: 2

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 3
<211> LENGTH: 236
<212> TYPE: PRT
<213> ORGANISM: Artificial Sequence
<220> FEATURE:
<223> OTHER INFORMATION: mCherry is a fluorescent marker protein derived from DsRed protein by mutagenesis.

<400> SEQUENCE: 3

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110
```

```
Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235


<210> SEQ ID NO 4
<211> LENGTH: 26
<212> TYPE: PRT
<213> ORGANISM: Artificial Sequence
<220> FEATURE:
<223> OTHER INFORMATION: It is a short peptide cloned from the
      ampicillin resistance gene of pcDNA3 plasmid with N-terminal extra
      four amino acids (YSDL).

<400> SEQUENCE: 4

Tyr Ser Asp Leu Met Ser Ile Gln His Phe Arg Val Ala Leu Ile Pro
1               5                   10                  15

Phe Phe Ala Ala Phe Cys Leu Pro Val Phe
            20                  25


<210> SEQ ID NO 5
<211> LENGTH: 19
<212> TYPE: PRT
<213> ORGANISM: Artificial Sequence
<220> FEATURE:
<223> OTHER INFORMATION: It is a short peptide cloned from the
      ampicillin resistance gene of pcDNA3 plasmid with N-terminal extra
      four amino acids (YSDL).

<400> SEQUENCE: 5

Tyr Ser Asp Leu Val Ala Leu Ile Pro Phe Phe Ala Ala Phe Cys Leu
1               5                   10                  15

Pro Val Phe


<210> SEQ ID NO 6
<211> LENGTH: 12
<212> TYPE: PRT
<213> ORGANISM: Artificial Sequence
<220> FEATURE:
<223> OTHER INFORMATION: It is a short peptide cloned from the
      ampicillin resistance gene of pcDNA3 plasmid with N-terminal extra
      four amino acids (YSDL).

<400> SEQUENCE: 6

Tyr Ser Asp Leu Ala Ala Phe Cys Leu Pro Val Phe
1               5                   10


<210> SEQ ID NO 7
<211> LENGTH: 8
<212> TYPE: PRT
```

<213> ORGANISM: Artificial Sequence
<220> FEATURE:
<223> OTHER INFORMATION: It is a short peptide cloned from the ampicillin resistance gene of pcDNA3 plasmid with N-terminal extra four amino acids (YSDL).

<400> SEQUENCE: 7

Tyr Ser Asp Leu Leu Pro Val Phe
1 5

<210> SEQ ID NO 8
<211> LENGTH: 26
<212> TYPE: PRT
<213> ORGANISM: Artificial Sequence
<220> FEATURE:
<223> OTHER INFORMATION: It is a short peptide cloned from the ampicillin resistance gene of pcDNA3 plasmid with N-terminal extra four amino acids (YSDL).

<400> SEQUENCE: 8

Tyr Ser Asp Leu Ala His Pro Glu Thr Leu Val Lys Val Lys Asp Ala
1 5 10 15

Glu Asp Gln Leu Gly Ala Arg Val Gly Tyr
20 25

<210> SEQ ID NO 9
<211> LENGTH: 26
<212> TYPE: PRT
<213> ORGANISM: Artificial Sequence
<220> FEATURE:
<223> OTHER INFORMATION: It is a short peptide cloned from the ampicillin resistance gene of pcDNA3 plasmid with N-terminal extra four amino acids (YSDL).

<400> SEQUENCE: 9

Tyr Ser Asp Leu Ile Glu Leu Asp Leu Asn Ser Gly Lys Ile Leu Glu
1 5 10 15

Ser Phe Arg Pro Glu Glu Arg Phe Pro Met
20 25

<210> SEQ ID NO 10
<211> LENGTH: 155
<212> TYPE: PRT
<213> ORGANISM: Homo sapiens

<400> SEQUENCE: 10

Met Ala Ala Gly Ser Ile Thr Thr Leu Pro Ala Leu Pro Glu Asp Gly
1 5 10 15

Gly Ser Gly Ala Phe Pro Pro Gly His Phe Lys Asp Pro Lys Arg Leu
20 25 30

Tyr Cys Lys Asn Gly Gly Phe Phe Leu Arg Ile His Pro Asp Gly Arg
35 40 45

Val Asp Gly Val Arg Glu Lys Ser Asp Pro His Ile Lys Leu Gln Leu
50 55 60

Gln Ala Glu Glu Arg Gly Val Val Ser Ile Lys Gly Val Cys Ala Asn
65 70 75 80

Arg Tyr Leu Ala Met Lys Glu Asp Gly Arg Leu Leu Ala Ser Lys Cys
85 90 95

Val Thr Asp Glu Cys Phe Phe Phe Glu Arg Leu Glu Ser Asn Asn Tyr
100 105 110

Asn Thr Tyr Arg Ser Arg Lys Tyr Thr Ser Trp Tyr Val Ala Leu Lys
115 120 125

-continued

```
Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155


<210> SEQ ID NO 11
<211> LENGTH: 203
<212> TYPE: PRT
<213> ORGANISM: Danio rerio

<400> SEQUENCE: 11

Met Ala Glu Ser Phe Lys Glu His Leu Gln Glu Ala Phe Glu Asp Leu
1               5                   10                  15

Gly Ala Asp Asn Leu Arg Lys Phe Lys Ser Lys Leu Gly Asp Arg Arg
            20                  25                  30

Gln Glu Pro Arg Val Thr Lys Ser Ala Ile Glu Lys Leu Lys Asp Glu
        35                  40                  45

Ile Asp Leu Ala Asp Leu Met Val Gly Val Phe Thr Ser Lys Asp Ala
    50                  55                  60

Val Ser Val Thr Val Glu Ile Leu Arg Ala Ile Lys Cys Ile Ala Val
65                  70                  75                  80

Ala Asp Asp Leu Leu Arg Asn Thr Gly Gln Ser Glu Ser Lys Gly Ala
                85                  90                  95

Pro Ser Asp Glu Ser Lys Cys Ala Ser Ser Lys Ala Val Ser Lys Val
            100                 105                 110

Ala Phe Ser Lys Val Asn Phe Ile Asp Glu His Trp Lys Glu Leu Ile
        115                 120                 125

Asp Arg Val Asn Asn Val Asp Pro Ile Leu Asp Ile Leu Arg Gln Lys
    130                 135                 140

Lys Val Ile Thr Asn Glu Asp Tyr Cys Thr Ile Arg Asn Lys Glu Thr
145                 150                 155                 160

Pro Gln Lys Lys Met Arg Glu Leu Leu Thr Gly Pro Ile Thr Cys Ala
                165                 170                 175

Gly Asn Lys Gly Lys Glu Val Leu Tyr Asp Ala Leu Arg Glu Ser Asn
            180                 185                 190

Lys Phe Leu Met Asp Asp Leu Glu Asp Ala Gln
        195                 200


<210> SEQ ID NO 12
<211> LENGTH: 30
<212> TYPE: DNA
<213> ORGANISM: Artificial Sequence
<220> FEATURE:
<223> OTHER INFORMATION: Synthetic Construct

<400> SEQUENCE: 12

atagagctca tggcggaatc tttcaaggag                                        30


<210> SEQ ID NO 13
<211> LENGTH: 27
<212> TYPE: DNA
<213> ORGANISM: Artificial Sequence
<220> FEATURE:
<223> OTHER INFORMATION: Synthetic Construct

<400> SEQUENCE: 13

agaattctac tgagcatcct caaggtc                                           27


<210> SEQ ID NO 14
```

-continued

```
<211> LENGTH: 85
<212> TYPE: DNA
<213> ORGANISM: Artificial Sequence
<220> FEATURE:
<223> OTHER INFORMATION: Synthetic Construct

<400> SEQUENCE: 14

tcgagtactc agatcttatg agtattcaac atttccgtgt cgcccttatt cccttttttg     60

cggcattttg ccttcctgtt ttttg                                           85


<210> SEQ ID NO 15
<211> LENGTH: 85
<212> TYPE: DNA
<213> ORGANISM: Artificial Sequence
<220> FEATURE:
<223> OTHER INFORMATION: Synthetic Construct

<400> SEQUENCE: 15

aattcaaaaa acaggaaggc aaaatgccgc aaaaaaggga ataagggcga cacggaaatg     60

ttgaatactc ataagatctg agtac                                           85
```

METHOD FOR ANTIGEN DELIVERY

FIELD OF THE INVENTION

Figure 1:
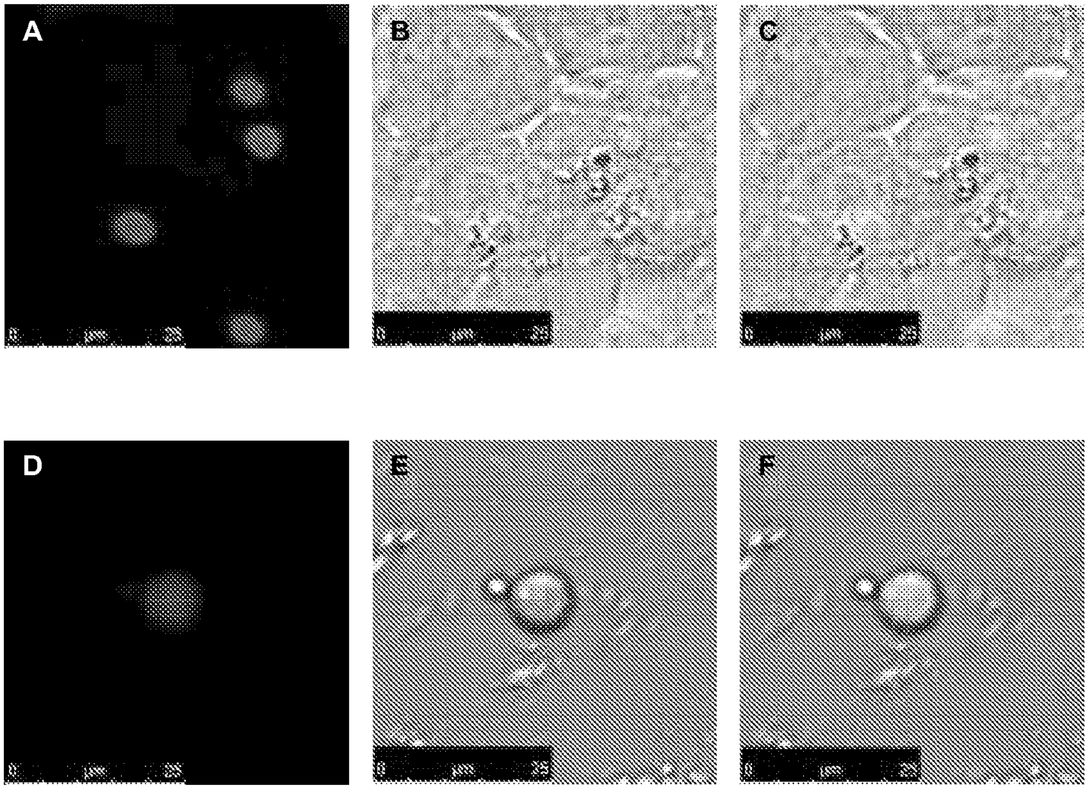

The present invention relates to a novel method for antigen and/or bioactive molecule delivery.

BACKGROUND

Traditionally, vaccines are based on the principle of body's antibody production against killed or live-attenuated pathogens. Recently, there are studies about developing subunit vaccines based on injecting particular components of a pathogen rather than injecting the whole pathogen itself, in order to improve biosafety. Subunit vaccines contain antigens in peptide or protein nature encoded by pathogens. In order to facilitate engulfment of these peptides and proteins by antigen presenting cells (APCs), antigens are loaded to nanometer or micrometer-sized particles. These types of vaccines are called particulate vaccines (De Temmerman et al., 2011).

There are ongoing studies about numerous antigen delivery methods to be used as particulate vaccines. Emulsions, liposomes, immunostimulant complexes, virus-like particles, gold, silica particles and polymer based particles are being used for this purpose. Polymer based particles can be based on either biodegradable compounds, such as poly(D, L-lactid) (PLA) and poly(D,L,lactic-co-glycolic acid) (PLGA) or non-biodegradable compounds, such as polystyrene. Layer-by-layer capsules, chitosan particles, micro- and nanogels are among the other polymer-based antigen delivery methods.

The common denominator of all the delivery methods mentioned above is to increase the size of an antigen to facilitate its engulfment by APCs (Xiang et al., 2006). Another property of particulate vaccines is to slow down the enzymatic degradation of the antigens either extracellularly or intracellularly after engulfment, in order to lengthen the time period for the antigens to stay in the environment and thereby enhance the capacity of APCs to present these antigens to T cells.

Methods similar to those employed for antigen delivery are being used in controlled drug release systems as well. There are applications where microparticulate drug release systems are employed via the oral or nasal routes. There are numerous studies about controlled release of growth factors from polymer based microparticles (Balmayor et al., 2011).

The efficient engulfment of antigens by APCs is of paramount importance in the process of antibody production. To achieve this, short peptide antigens (haptens) are cross-linked to bigger carrier proteins. The most frequently used carrier proteins for this purpose are limpet hemocyanin (KLH) and bovine serum albumin (BSA) proteins. The most preferred carrier protein KLH is a 350 kDa molecular weight protein isolated from *Megathura crenulata*. This protein has a tendency to aggregate. Both soluble and aggregate forms of KLH show antigenic properties. Due to its big size, expression of KLH protein in bacteria or fusion of hapten and KLH coding sequences by molecular cloning methods is not practical.

Among the antigen and/or drug delivery systems mentioned above, liposomes and hydrogels degrade relatively fast. Besides, liposomes also tend to fuse with each other. Thus, both liposomes and hydrogels have short shelf-lives.

Methods that are used in the synthesis of polymer based microparticles (organic solvents, high temperature and freeze-thaw cycles) may damage the structure and activity of the antigen or bioactive molecule payload.

In general, subunit vaccines yield a lower amount of antibody production compared to whole-pathogen vaccines. Various strategies have been developed to overcome this problem. The first approach is to coat microparticles with molecules that have the tendency to fuse with APC membranes (antibodies, receptor ligands). In this way, the frequency of microparticles' engulfment by APCs is increased. Another strategy is to coat the microparticles with molecules (adjuvants) targeting specific APC receptors which enhance the antigen presentation capability of APCs. Toll-like receptor (TLR) family members are stimulated upon binding to their ligands and pathways that promote cells' antigen presentation capability are activated. In order to stimulate TLR family members, microparticles are covered with CpG, poly(I:C), MPL, 3M-019 and flagellin ligands.

Apoptosis-associated speck-like protein containing a CARD (ASC, PYCARD, TMS1) is a 22 kDa adaptor protein with a PYD domain at N-terminal and CARD domain at C-terminal that functions in NLRP3, NLRC4 and AIM2 inflammasome complexes. ASC protein has a role in the activation of caspase-1 protein in inflammatory and pyroptotic signaling pathways (Franchi et al., 2009). It is a cytoplasmic protein that forms a speck structure (ASC speck) in the perinuclear space upon activation of inflammasome complexes (Miao et al., 2011).

During pyroptotic cell death, upon arrival of a proinflammatory stimulus ASC proteins form spherical supramolecular structures that are several micrometers in diameter called pyroptosomes. Presumably, pyroptosomes are formed by oligomerized ASC dimers (Fernandes-Alnemri et al., 2007).

The NLRP3 inflammasome, which also contains the ASC protein, can be triggered by stimuli such as extracellular ATP, membrane damaging toxins (nigericin), lysosomal damage, monosodium urea (MSU) and UV rays. NLRP3 inflammasome activation is accompanied by the synthesis of micrometer-sized speck or pyroptosome structures. Such speck structures can also be synthesized inside cells upon the overexpression of the ASC protein, without the need for any other stimulus. ASC specks can be synthesized in vitro by incubating purified recombinant ASC protein in a hypotonic solution at 37° C. (Fernandes-Alnemri et al., 2007).

In the international patent document WO2009014863, the ASC protein and the pyroptosome are used in the diagnosis and treatment of autoimmune diseases. According to this invention, apoptosis and pyroptosome structures containing ASC dimers and procaspase-1 occur during the early inflammatory response in macrophage cells. Caspase-1 activation is dependent on pyroptosome formation. The state of inflammation is diagnosed by isolating pyroptosomes from macrophage cells.

After MF59-adjuvanted influenza vaccination, it was postulated that the ASC protein plays a role in triggering antigen specific humoral response, according to data comparisons between ASC knock-out and wild type mice. However, no suggestion was made about achieving antigen delivery by binding antigen peptides to ASC protein or ASC specks (Ellebedy et al., 2011).

SUMMARY OF THE INVENTION

The objective of the present invention is to provide loading the ASC speck carrier with antigens and/or bioactive molecules.

Another objective of the present invention is to provide using the ASC speck carrier in the delivery of antigens and/or bioactive molecules to antigen presenting cells (APCs).

A further objective of the present invention is to slow down the degradation of antigens endocytosed or phagocytosed together with the ASC speck carrier by enzymes inside cells and to lengthen the time period antigens stay in the environment and thereby enhance the antigen presentation capacity of APCs to T cells.

Another objective of the present invention is to increase the size of antigens and/or bioactive molecules via the ASC speck carrier in order to facilitate their engulfment by APCs.

Yet another objective of the present invention is to increase the shelf-life of antigens and/or bioactive molecules carried by the ASC speck carrier.

DETAILED DESCRIPTION OF THE INVENTION

A method for antigen delivery developed to fulfill the objectives of the present invention is illustrated in the accompanying figures wherein;

FIG. 1—Synthesis of mCherry-ASC specks in HEK 293 FT cells and their purification. HEK 293 FT cells were transfected with a plasmid encoding mCherry-ASC fusion protein. A, B, C: HEK 293 FT cells synthesizing mCherry-ASC specks. A: mCherry-ASC specks (confocal microscopy) B: Cells under bright field microscopy. C: Overlay of FIGS. 1A and 1B. Synthesized mCherry-ASC specks were later purified from HEK 293 FT cells. D: Purified mCherry-ASC specks (confocal microscopy). E: Specks under bright field microscopy F: Overlay of FIGS. 1D and 1E.

Figure 2:
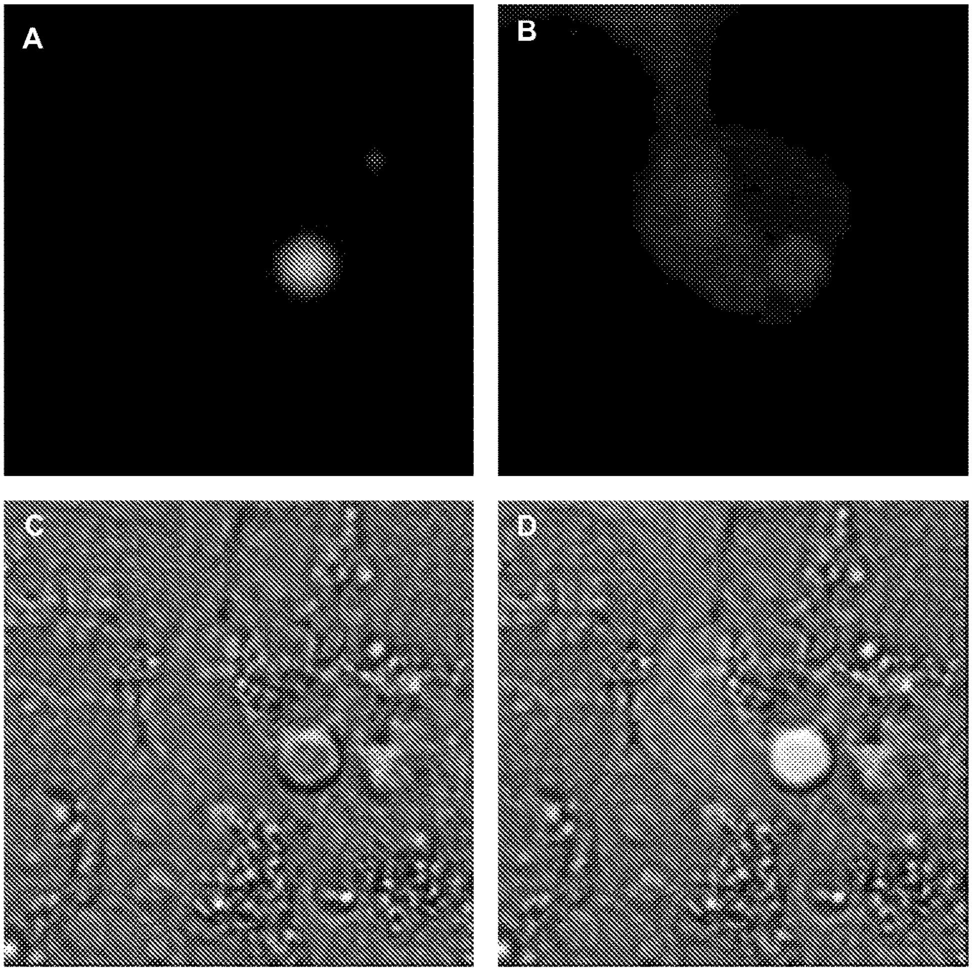

FIG. 2—Loading of mCherry-FGF2 fusion proteins to EGFP-ASC specks. Plasmids encoding mCherry-FGF2 and EGFP-ASC fusion proteins were transfected into HEK 293 FT cells and loading of mCherry-FGF2 fusion proteins to EGFP-ASC specks was observed. A: EGFP-ASC B: mCherry-FGF2 C: Bright field microscopy image D: Overlay of FIGS. 2A, 2B and 2C.

Figure 3:
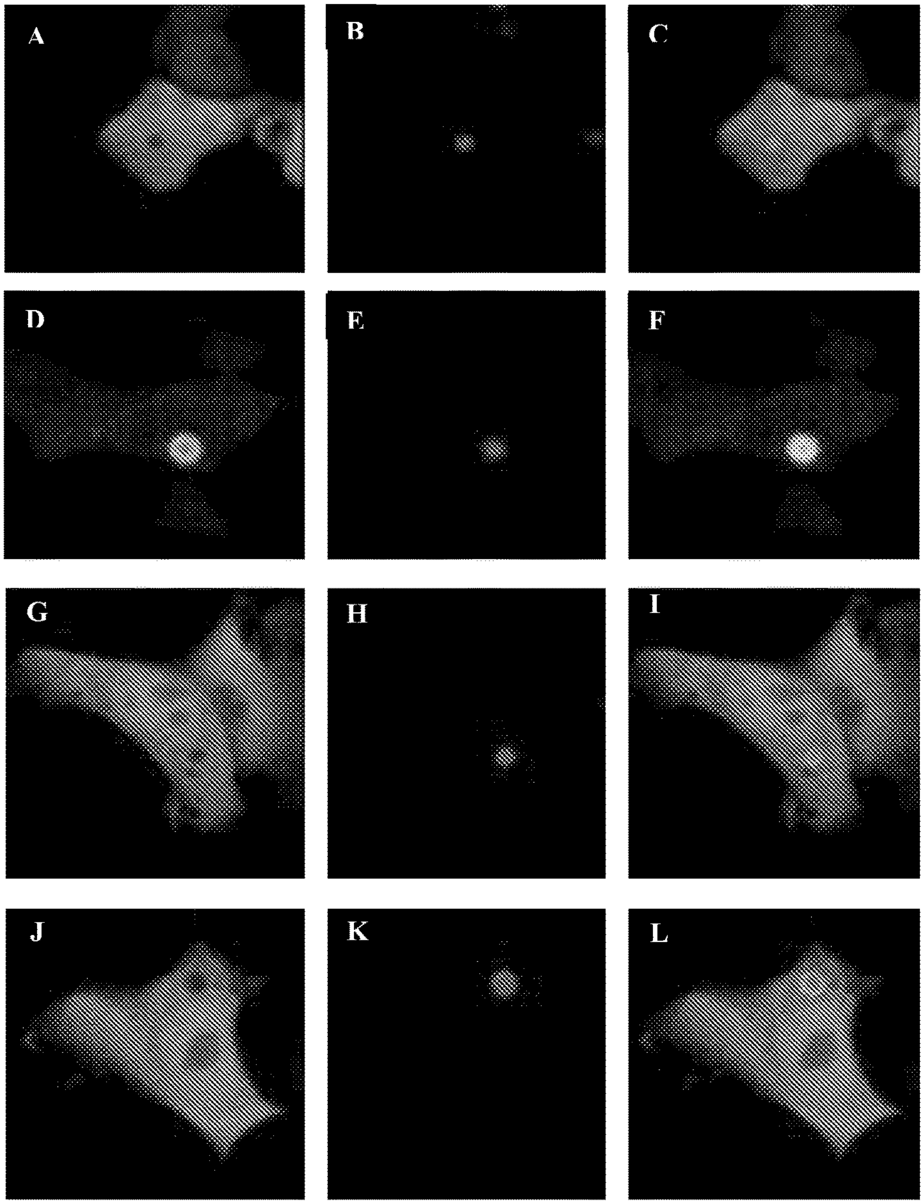

FIG. 3—Coating of mCherry-ASC specks' outer shell with peptides fused to EGFP protein via hydrophobic interactions. HEK 293 FT cells were co-transfected with plasmids encoding mCherry-ASC and EGFP-X. X is for 3A, 3B, 3C: "stop" (EGFP-stop, SEQ ID NO: 2); 3D, 3E, 3F: Peptide 1 (SEQ ID NO: 4); 3G, 3H, 3I: Peptide 2 (SEQ ID NO: 8); 3J, 3K, 3L: Peptide 3 (SEQ ID NO: 9). 3A, 3D, 3G, 3J: EGFP-X (X: "stop", Peptide 1, Peptide 2, Peptide 3, respectively). 3B, 3E, 3H, 3K: mCherry-ASC. 3C, 3F, 3I, 3L: Overlay of EGFP-X (X: "stop", Peptide 1, Peptide 2, Peptide 3, respectively) and mCherry-ASC proteins.

Figure 4:
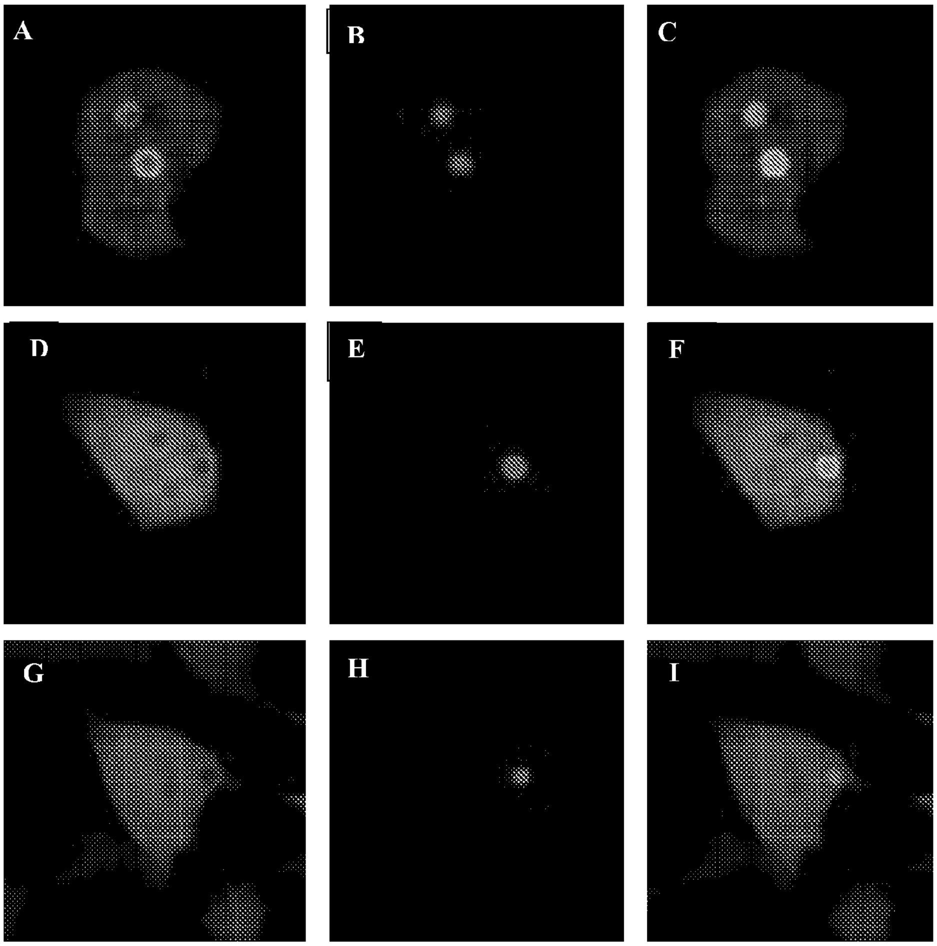

FIG. 4—Hydrophobic peptides should be at least 13 amino acids long to coat the outer shell of mCherry-ASC specks. Plasmids encoding EGFP-X were co-transfected to HEK 293 FT cells. X is for 4A, 4B, 4C: Peptide 1_19aa (SEQ ID NO: 5); 4D, 4E, 4F: Peptide 1_12aa (SEQ ID NO: 6); 4G, 4H, 4I: Peptide 1_8aa (SEQ ID NO: 7). 4A, 4D, 4G: EGFP-X. 4B, 4E, 4H: mCherry-ASC. 4C, 4F, 4I: Overlay of EGFP-X (X: Peptide 1_19aa, Peptide 1_12aa, Peptide 1_8aa, respectively) and mCherry-ASC proteins.

Figure 5:
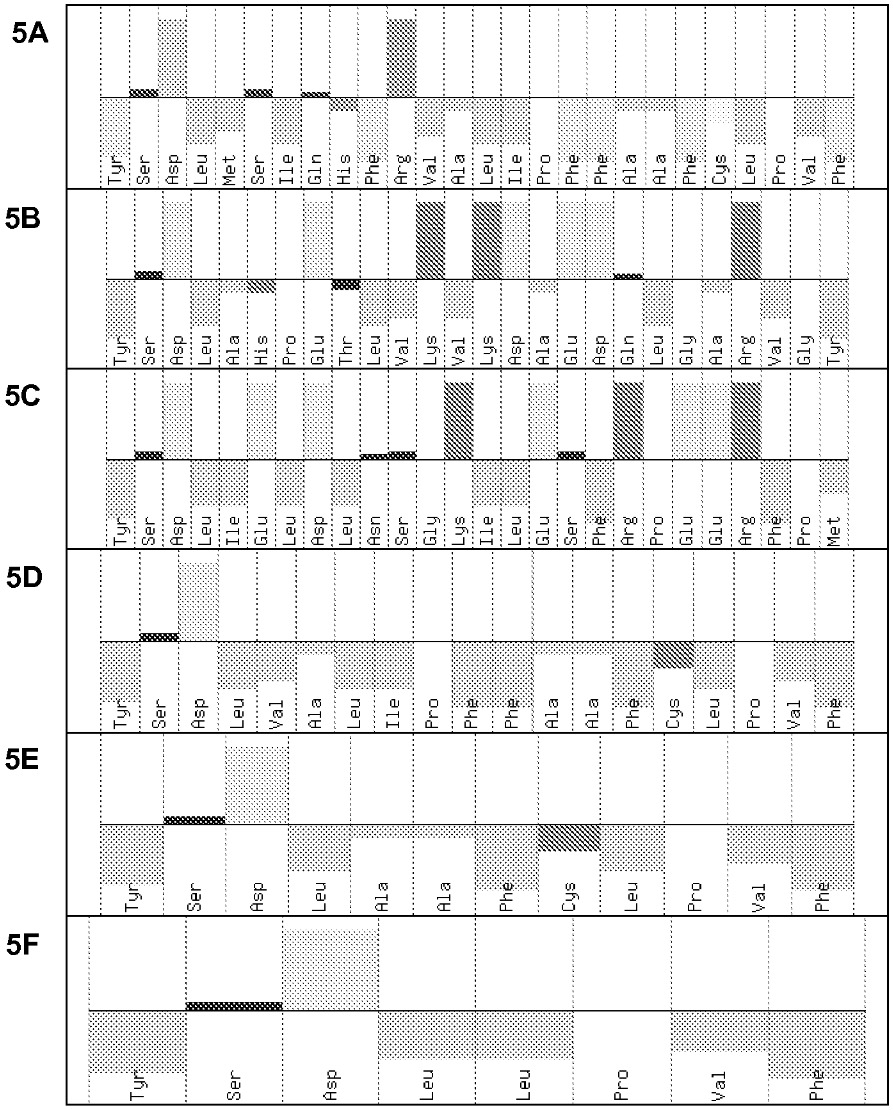

FIG. 5—Hydropathy graphs of peptides fused to EGFP. Descending columns below the horizontal line represent hydrophobic amino acids while ascending columns represent hydrophilic amino acids. 5A: Peptide 1 (SEQ ID NO: 4), 5B: Peptide 2 (SEQ ID NO: 8), 5C: Peptide 3 (SEQ ID NO: 9), 5D: Peptide 1_19aa (SEQ ID NO: 5), 5E: Peptide 1_12aa (SEQ ID NO: 6), 5F: Peptide 1_8aa (SEQ ID NO: 7).

Figure 6:
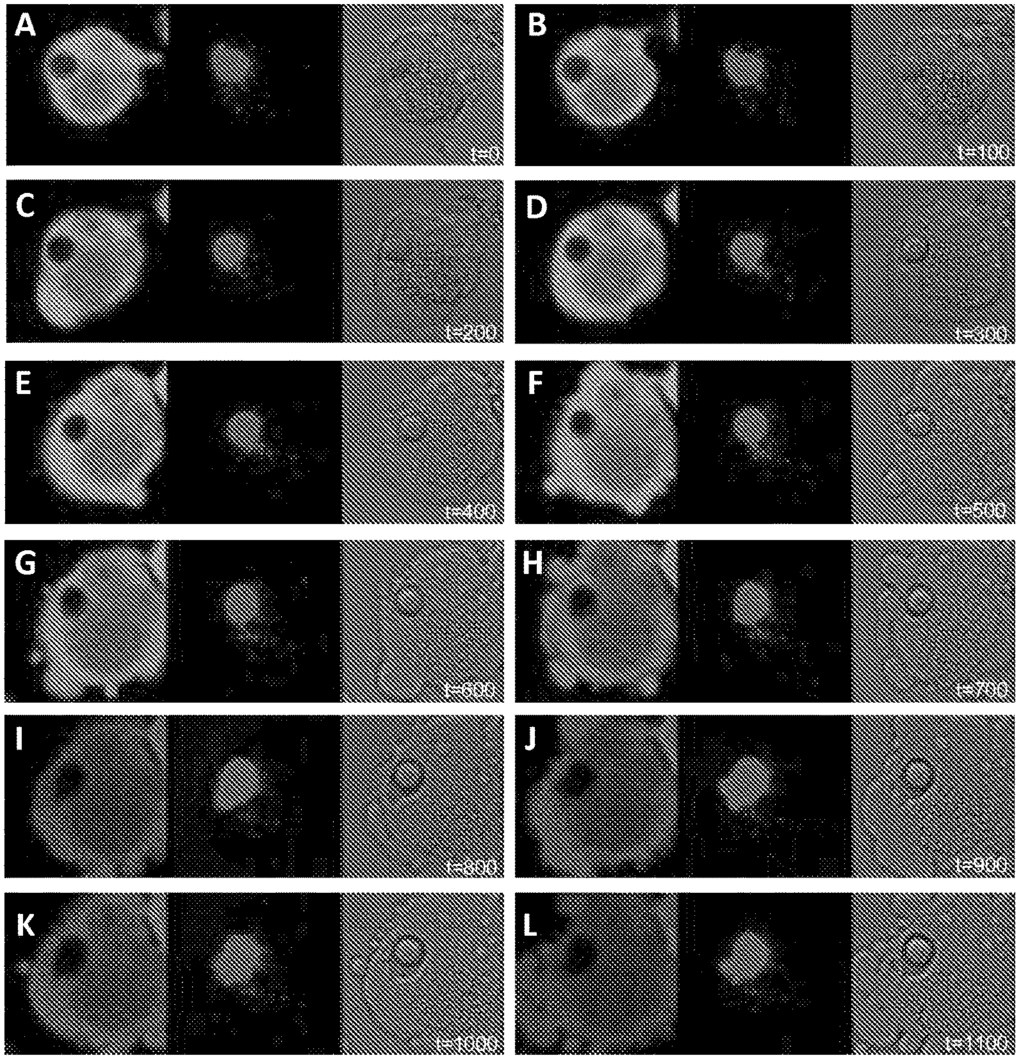

FIG. 6—Membrane enclosed state of mCherry-ASC specks engulfed by THP-1 cells and their slow degradation inside the cell. PMA differentiated THP-1 EGFP-ASC stable cell line with macrophage characteristics was incubated with purified mCherry-ASC specks for 2 hours. In the course of extensive time-lapse imaging in an unphysiological environment, cells lost their membrane integrity and showed apoptotic characteristics. The membrane structure of the phagolysosome organelle containing the mCherry-ASC speck carrier was relaxed due to apoptosis and could be clearly observed. Besides, the space inside the phagolysosome but outside of the mCherry-ASC speck was filled with mCherry signal 6G-L: t=600 s to t=1100 s). This showed that mCherry-ASC specks were degraded at a slow pace intracellularly. The cells were imaged under confocal microscopy in 100 second intervals (6A-6L). Left: EGFP-ASC. Middle: mCherry-ASC. Right: Bright field.

Figure 7:
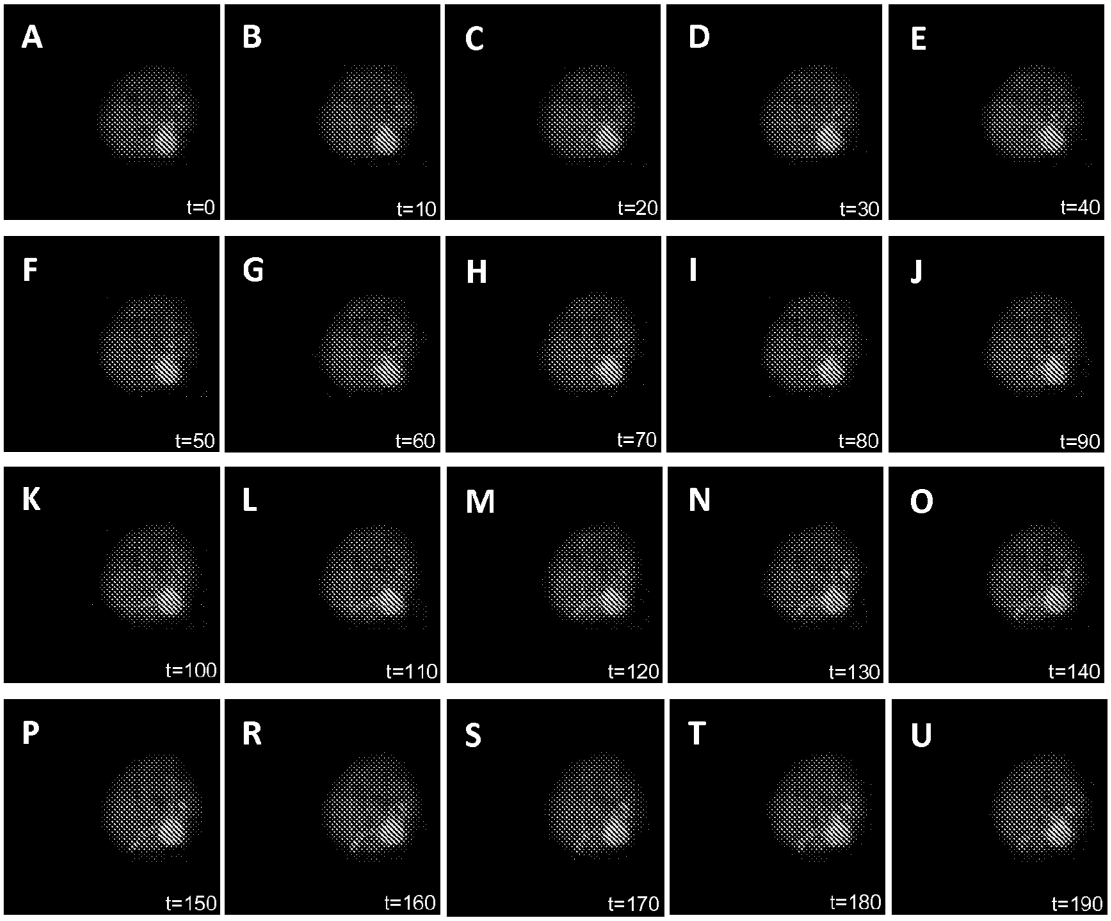

FIG. 7—Tubular vesicles' pinching-off from the phagolysosomes containing mCherry-ASC speck. PMA differentiated THP-1 EGFP-ASC stable cell line with macrophage characteristics was incubated with purified mCherry-ASC specks for 2 hours. The moment of tubular vesicles' pinching-off from the phagolysosome containing mCherry-ASC speck, engulfed by THP-1 cells, was observed. Total degradation of specks did not take place while the cells were being observed. The cells were imaged under confocal microscopy in 10 second intervals (7A-7U).

Figure 8:
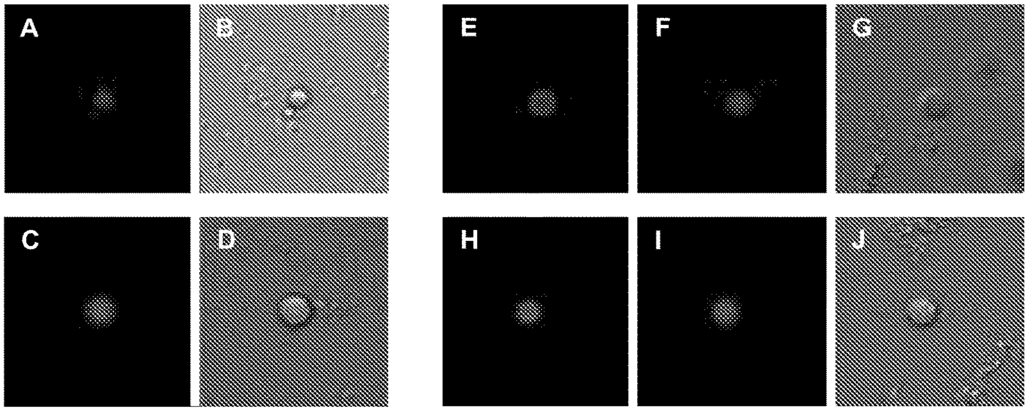

FIG. 8—Endurance of mCherry-ASC specks against prolonged incubation at 37° C. mCherry-ASC specks were synthesized in HEK 293 FT cells and purified. Aliquots taken from mCherry-ASC specks were examined under confocal microscopy right after purification (8A, 8B) and 30 days after incubation at 37° C. (8C, 8D). mCherry-ASC and EGFP-Peptide 1 (Peptide 1, SEQ ID NO: 4) encoding plasmids were co-transfected into HEK 293 FT cells. Aliquots taken from mCherry-ASC specks purified from the co-transfected cells were examined under confocal microscopy right after purification (8E-8G) and 30 days after incubation at 37° C. (8H-8J). It was observed that EGFP-Peptide 1 was coating the outer shell of mCherry-ASC specks and remained bound to mCherry-ASC specks even after the prolonged incubation.

Figure 9:
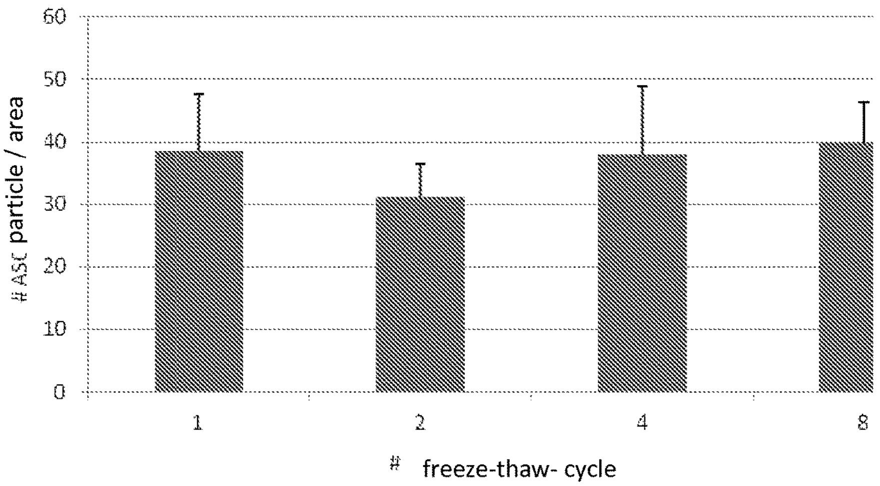

FIG. 9—Endurance of mCherry-ASC specks against repeated freeze-thaw cycles. mCherry-ASC specks were synthesized in HEK 293 FT cells, purified and subjected to repeated freeze-thaw cycles from −80° C. to +37° C. Aliquots taken from freeze-thawed preparations were counted under confocal microscopy. Even after 8 freeze-thaw cycles, no significant changes were observed in the mCherry-ASC speck counts.

The composition functioning in antigen and/or bioactive molecule delivery in its simplest form contains;

- at least one ASC speck carrier formed by ASC proteins coming together,
- at least one peptide/protein, being the antigen and/or the bioactive molecule, carried by the ASC speck carrier.

"Apoptosis-associated speck-like protein containing a CARD" and "ASC" stands for expression products of ASC gene's homologues in different species and its isoforms. This definition is valid for homologues of ASC protein in human (SEQ ID NO: 1) and zebrafish (SEQ ID NO: 11) species and all other living beings.

ASC specks are defined as micron-sized perinuclear aggregates formed by ASC proteins as described above.

These structures can be synthesized upon stimulation of NLRP3, AIM2 and NLRC4 proteins and/or triggering of pyroptosis (Miao et al., 2011, Leemans et al., 2011, Gross et al., 2011). However, ASC speck structures can be synthesized upon overexpression of the ASC protein (SEQ ID NO: 1) without need for any other stimuli. In this invention, "ASC speck carrier", "ASC speck" and "speck" expressions stand for any kind of aggregate synthesized from ASC proteins (SEQ ID NO: 1) in cell culture (endogenous, stable or transient gene expression) or aggregates synthesized in vitro from purified ASC proteins (SEQ ID NO: 1), produced in bacterial, yeast, baculoviral etc. gene expression systems.

In the inventive composition, at least one peptide/protein being the antigen carried by the ASC speck carrier, briefly antigen; is at least one member of the group consisting of peptides, proteins and peptides mimicking carbohydrates or a mixture of at least two members of these groups stimulating antibody production upon entering into the body.

Bioactive molecules are molecules that have therapeutic effects on a living organism, tissue or cell. In the inventive composition, at least one peptide/protein being bioactive molecule carried by the ASC speck carrier, briefly bioactive molecule; is at least one member of the group consisting of drugs, enzymes, growth factors, hormones, receptors, receptor ligands, adjuvants and antibodies or a mixture of at least two members of these groups.

In the preferred embodiment of the present invention, a composition comprises at least one type of antigen and/or at least one type of bioactive molecule.

The ASC speck carrier can carry antigens and/or bioactive molecules in different ways. In other words, antigens and/or bioactive molecules can be loaded to the ASC speck carrier in different ways.

In the preferred embodiment of the present invention, a DNA sequence encoding an antigen and a DNA sequence encoding the ASC protein are combined in a way that a fused DNA sequence encoding both antigen and ASC protein is created and this fused DNA sequence encodes an ASC-antigen fusion protein containing both antigen and ASC protein.

Due to the relatively small 22 kDa size of the ASC protein, molecular cloning and subsequent expression of ASC-antigen fusion proteins in cell culture or bacteria are extremely efficient.

In the preferred embodiment of the present invention, at least one ASC protein forming the ASC speck carrier and antigen exist as a fusion protein and in this way, the antigen is carried with the ASC speck carrier as a fusion protein in the inventive composition.

Purification of ASC specks from cell culture and their in vitro synthesis were described before (Fernandes-Alnemri et al., 2007). Purification and in vitro synthesis of the inventive composition were carried out according to methods described in the said paper.

The inventive composition, comprising the ASC speck carrier and antigens fused to ASC proteins forming the ASC speck carrier, is synthesized in cell culture and purified from cell culture.

In an alternative embodiment of the present invention, ASC-antigen fusion proteins produced in bacteria (or another gene expression system) are purified and the inventive composition, comprising the ASC speck carrier and antigens fused to ASC proteins forming the ASC speck carrier, is synthesized in vitro.

An antigen existing as a fusion protein with the ASC protein can be inserted at the N-terminus, C-terminus or inside the ASC protein. In this embodiment of the invention, the antigen is carried inside the ASC speck carrier.

In another preferred embodiment of the present invention, antigens and/or bioactive molecules can be loaded to the ASC speck carrier by forming hydrophobic interactions with the ASC speck carrier or the ASC proteins forming the ASC speck carrier.

In the preferred embodiment of the present invention, peptide or protein sequences, being the antigen or the bioactive molecule loaded to ASC speck carrier via hydrophobic interactions, are at least 13 amino acids long and hydrophobic. Peptide or protein sequences, being the antigen or the bioactive molecule, are referred to as hydrophobic when their mean hydrophobicity value is above 0 or hydrophilic when their mean hydrophobicity value is below 0.

Antigens or bioactive molecules with hydrophilic properties cannot be carried with ASC speck carriers via hydrophobic interactions alone. Antigens or bioactive molecules with hydrophilic properties can be loaded to the ASC speck carrier via hydrophobic interactions by creating a fusion protein of antigen and/or bioactive molecule with a peptide comprising at least 13 amino acids long and hydrophobic sequence.

In this preferred embodiment of the invention, antigens and/or bioactive molecules coat the surface or in other words, the outer shell of the ASC speck carrier.

The inventive composition comprising the ASC speck carrier and at least one antigen and/or bioactive molecule loaded to the ASC speck carrier via hydrophobic interactions is synthesized in cell culture and purified from cell culture.

In an alternative embodiment of the present invention, bacterially-produced (or produced via another gene expression system) ASC proteins forming the ASC speck carrier and an antigen and/or a bioactive molecule are purified; and the inventive composition comprising the ASC speck carrier and at least one antigen and/or bioactive molecule, loaded to the ASC speck carrier via hydrophobic interactions, is synthesized in vitro.

In the preferred embodiment of the present invention, the composition is formed by loading at least one antigen and/or bioactive molecule to the ASC speck carrier via hydrophobic interactions and is named as a composition via hydrophobic interactions.

In another preferred embodiment of the present invention, the composition is formed by forming a fusion protein of at least one antigen and/or bioactive molecule with ASC proteins forming the ASC speck carrier and is named as fused-composition.

In another preferred embodiment of the present invention, the composition is formed by both fused-composition and composition via hydrophobic interactions production methods. This composition is named as fused-composition via hydrophobic interactions.

The inventive composition can be synthesized in cell culture with or without any stimulus. The said stimuli are achieved by proinflammatory stimuli.

In the inventive composition, the ASC speck carrier is synthesized by the overexpression of a plasmid containing a DNA sequence encoding the ASC protein (SEQ ID NO: 1) in cell culture without any stimulus. In this way, the ASC speck carrier and the antigen and/or the bioactive molecule carried by the ASC speck carrier form the inventive composition in cell culture without any stimulus.

In another preferred embodiment of the present invention, the ASC speck carrier in the inventive composition can be synthesized by the stimulation of cells with proinflammatory stimuli. In this way, the ASC speck carrier and the antigen and/or the bioactive molecule carried by ASC speck carrier form the inventive composition in cell culture with a stimulus. The said proinflammatory stimulus can be any NLRP3, NLRC4 or AIM2 inflammasome triggering stimulus. The NLRP3 inflammasome can be triggered by monosodium urea (MSU), uric acid, asbestos, silica, aluminium hydroxide, ATP, plasma membrane damaging substances, such as nigericin, UVB, hyaluronan, amyloid-β fibers, calcium pyrophosphate dehydrate crystals; the NLRC4 inflammasome can be triggered by flagellin and the AIM2 inflammasome can be triggered by cytosolic DNA or DNA analogs (polyA:T) (Franchi et al., 2009, Jin et al., 2010).

In another embodiment of the present invention, the composition is synthesized in a hypotonic solution in vitro. ASC proteins forming the ASC speck carrier (SEQ ID NO: 1), the antigen and/or bioactive molecule are expressed in bacterial, yeast, baculoviral, etc. gene expression systems and then purified. The purified ASC protein and the antigen and/or bioactive molecule form the inventive composition by incubation together in a hypotonic solution (solution having <50 mM KCl) at 37° C.

The said methods for antigen loading are valid for the human ASC protein (SEQ ID NO: 1) and its homologues in evolutionarily closely related species as well as its homologues in distant species such as zebrafish (zASC, SEQ ID NO: 11). Speck structures formed by zASC protein were described before (Masumoto et al., 2003).

In a preferred embodiment of the present invention, when the composition is intended to be used in the development of a polyclonal antibody against an antigen that belongs to humans or a living being evolutionarily closely related to humans, then it is advisable to use the ASC protein in a distant relative such as the zebrafish homologue of the ASC protein (SEQ ID NO: 11). In this way, even if the host organism used in the antibody production develops antibodies against the zebrafish homologue of the ASC protein (SEQ ID NO: 11), due to the high sequence diversity between human and zebrafish ASC proteins, the likelihood of these antibodies recognizing the human ASC protein (SEQ ID NO: 1) is decreased. Similarly, when the composition is intended to be used in the development of a polyclonal antibody against an antigen belonging to zebrafish or its close relative, then it is advisable to use a relatively distant homologue such as the human homologue of the ASC protein (SEQ ID NO: 1). Human (SEQ ID NO: 1) and zebrafish (SEQ ID NO: 11) ASC proteins share 34.2% sequence identity and only 5 amino acids in a row are identical. These similarities can be reduced by making at least one or few mutations in the sequence.

The inventive composition provides delivery of antigens and/or bioactive molecules together with the ASC speck carrier to antigen presenting cells (APCs). Antigen presenting cells (APCs) are macrophages, dendritic cells and B cells.

APCs engulf the inventive composition into cells via endocytosis/phagocytosis. The engulfed composition is enclosed by an endosomal/phagosomal vesicle (early endosome) derived from cells' membrane with pH value between 6-6.5 and thereby the composition enters into the endocytic/phagocytic pathway. The endocytic/phagocytic pathway consists of the early endosome (pH=6-6.5), endolysosome/phagolysosome (pH=5-6) and lysosome (pH=4.5-5) stages, progressively. The composition is degraded at the endolysosome/phagolysosome and lysosome stages by hydrolytic enzymes and acidic pH values. As a result, any antigen contained in the composition is degraded into 13-18 amino acid long oligopeptides and these peptides are loaded to MHC class II molecules and delivered to the plasma membrane in a complex. $T_H$ cells recognize and interact with these antigenic piece-MHC class II structures.

Engulfed antigens together with the inventive composition are degraded via the endocytic/phagocytic pathway in a controlled manner. In this way, the composition provides a relatively slow antigen release and degradation.

While endocytosed/phagocytosed ASC specks were inside the phagolysosome organelle, tubular vesicles' pinching-off from the organelle was clearly observed. It is known that oligopeptides, the degradation products of proteins inside phagolysosomes, are loaded to MHC class II molecules in this type of vesicles.

Ideal vaccines are designed to have a long shelf-life, to be resistant to freeze-thaw cycles that could happen during transportation or by accident and to preserve their integrity at body temperature for long intervals, while being biodegradable at the same time.

By means of the inventive composition, the stability of antigens and/or bioactive molecules in the composition increases at 37° C. and the antigen/bioactive molecule can endure without degradation for at least 30 days inside the composition at this temperature. The inventive composition thereby enhances the stability of an antigen under physiological conditions and lengthens its shelf-life.

By means of the inventive composition, an antigen can endure at least 8 freeze-thaw cycles without degradation. Thereby, the composition minimizes any damage the antigen/bioactive molecule could sustain from freeze-thaw events that could happen during transportation or by accident.

Processes harmful to antigens such as high temperature, organic solvent usage or freeze-thawing are eliminated with the inventive composition.

All descriptions mentioned above about a composition containing ASC speck carrier and antigens is also valid for a composition containing the ASC speck carrier and bioactive molecules.

Various applications can be developed around these basic concepts using the method for antigen delivery of this invention and the invention cannot be limited to the examples given here, the invention is essentially as defined in the claims.

SPECIFIC EMBODIMENTS

Example 1

Synthesis of the composition containing the ASC speck carrier and mCherry proteins fused to ASC proteins forming the ASC speck carrier in HEK 293 FT cells and its purification from HEK 293 FT cell culture.

The DNA sequence encoding an antigen or a bioactive molecule in peptide or protein nature, is cloned into a plasmid containing ASC protein (SEQ ID NO: 1) coding sequence in a way that they will form a fusion protein. The plasmid should preferably contain an SV40 origin of replication (e.g. pcDNA3 or pEGFP-C3 vector backbone). The plasmid created accordingly is transfected into a selected cell line in order to overexpress the ASC-antigen (or bioactive molecule) fusion protein. HEK 293 FT cell line was used in this invention because it multiplies SV40 origin of replication containing plasmids in high copy numbers inside the cells.

pmCherry-C3.1-ASC plasmid encoding mCherry-ASC fusion protein was transfected into HEK 293 FT cells by calcium-phosphate method. 1 million cells were plated on a 35 mm cell culture dish a day before transfection. 1 μg plasmid was added up to 219 μl volume with distilled water and mixed with 31 μl 2M CaCl2. 250 μl 2×HBS (280 mM NaCl, 50 mM HEPES, 1.5 mM Na2HPO4, pH=7.05) was added, mixed and the mixture was incubated for 15 minutes at room temperature. The mixture was added dropwise onto HEK 293 FT cells plated on the previous day. Alternatively, the transfection mixture can be added just after the cells were plated and before they attach to the culture dish.

When the ASC protein was overexpressed in HEK 293 FT cells, ASC specks were synthesized without the need for a stimulus. When peptides or proteins fused to the ASC protein (e.g. mCherry-ASC) forming the ASC speck carrier were overexpressed in HEK 293 FT cells, they formed the inventive composition with the ASC speck carrier as a fusion protein without a stimulus (FIG. 1A-C).

The composition composed of the ASC speck carrier and mCherry proteins fused to ASC proteins forming the ASC speck carrier in HEK 293 FT cells was shown under confocal microscopy (FIG. 1A), bright field microscopy (FIG. 1B) and overlay of confocal and bright field microscopy images (FIG. 1C).

A detailed protocol about purification of ASC specks from cell culture was described before (Fernandes-Alnemri et al., 2007). In our invention, purification of the inventive composition was carried out based on this protocol. HEK 293 FT cells containing the composition were collected in Triton X-100 buffer solution with protease inhibitor cocktail (1% Triton X-100, 150 mM NaCl, 2 mM EDTA, 20 mM Tris-HCl, pH=7.5) and passed through a G22 needle tip 20 times. The obtained lysate was centrifuged at 5000 rpm for 1 minute and soluble proteins in the supernatant were discarded. Later, the pellet was resuspended in 1×PBS (137 mM NaCl, 2.7 mM KCl, 4.3 mM Na2HPO4, 1.47 mM KH2PO4) solution. Optionally, the resuspended pellet can be passed through a 5 μm filter.

The composition obtained after this process composed of the ASC speck carrier and mCherry proteins fused to ASC proteins forming the ASC speck carrier was shown under confocal microscopy (FIG. 1D), bright field microscopy (FIG. 1E) and overlay of confocal and bright field microscopy images (FIG. 1F) in vitro.

Both inside the cell and in vitro, mCherry protein was present in the ASC speck carrier as a fusion protein (FIG. 1A, 1D).

Example 2

Synthesis of a fused DNA sequence encoding the mCherry-ASC fusion protein.

In order to clone pmCherry-C3.1-ASC plasmid that encodes for mCherry-ASC fusion protein, the DNA sequence encoding the human ASC protein was obtained from pcDNA3-ASC plasmid by digesting with HindIII-EcoRI enzymes and ligated to the multiple cloning site of pmCherry-C3.1 vector digested with same enzymes to create an mCherry-ASC fusion protein coding sequence. The pcDNA3-ASC plasmid was a gift from Gabriel Nunez (University of Michigan, Ann Arbor, USA).

In order to clone pmCherry-C3.1 plasmid, the mCherry protein coding sequence was PCR amplified from pcDNA3 IFP 1.4 plasmid using primers NheI_mCherry_F (gctagcaccatggtgtctaagggcgaaga) and XhoI_mCherry_R (ctcgagtttcttgtacagctcgtccat). The EGFP protein coding sequence was digested and removed from the pEGFP-C3 plasmid by NheI-XhoI enzymes and PCR product digested with same enzymes was ligated to its place. pcDNA3 IFP 1.4 was a gift from Tsien Lab (University of California San Diego, San Diego, USA).

A fusion protein can be created by cloning the preferred antigen/bioactive molecule coding sequence to the N-terminus of ASC protein (SEQ ID NO: 1) coding sequence as in the mCherry-ASC fusion protein example or alternatively to the C-terminus or inside the protein coding sequence.

Example 3

Alternative methods of loading antigens and/or bioactive molecules to the ASC speck carrier.

FGF2 (fibroblast growth factor 2, SEQ ID NO: 10) loaded to the ASC speck carrier was given as an example of bioactive molecules which can be loaded to the ASC speck carrier. The FGF2 protein is a growth factor known to have role in angiogenesis, embryonic development and wound healing.

When it is desirable to load an antigen or a bioactive molecule to ASC specks without creating a fusion protein with the ASC protein (SEQ ID NO: 1), the plasmid containing the DNA sequence encoding the antigen and/or the bioactive molecule and the plasmid containing the DNA sequence encoding the ASC protein are co-transfected into the preferred cell line.

As an example, the plasmid encoding mCherry-FGF2 fusion protein was co-transfected with the plasmid encoding EGFP-ASC fusion protein. A mixture of mCherry-FGF2 and EGFP-ASC encoding plasmids, 1 μg each, were mixed in a total 219 μl volume in distilled water. The rest of the transfection procedure and the purification of the inventive composition comprising ASC speck carrier and the antigen and/or bioactive molecule were carried out as in Example 1.

The inventive composition consisting of the ASC speck carrier, EGFP proteins (antigen) fused to ASC proteins forming the ASC speck carrier and the mCherry-FGF2 protein (bioactive molecule) coating the outer shell of the ASC speck carrier in HEK 293 FT cells were shown under confocal microscopy (FIG. 2A-B), bright field microscopy (FIG. 2C) and overlay of confocal and bright field microscopy images (FIG. 2D).

It can be observed that a spherical shell composed of mCherry-FGF2 fusion proteins coats the outer shell of the ASC speck carrier composed of the EGFP-ASC fusion proteins in cells imaged under confocal microscopy (FIG. 2). In this figure and all other figures, EGFP was shown in green, mCherry was shown in red and the overlapping signal in merged images of these proteins was shown in yellow.

The inventive composition is capable of comprising more than one type of peptide or protein in different ways. The inventive composition is able to carry at least one peptide/protein or at least one type of peptide/protein coating its outer shell while at least one peptide/protein or at least one type of peptide/protein inside the ASC speck.

Any interaction between mCherry (SEQ ID NO: 3), EGFP (SEQ ID NO: 2), ASC specks composed of ASC proteins (SEQ ID NO: 1) and FGF2 protein (SEQ ID NO: 10) have not been reported to date.

Example 4

Production of fused DNA sequences encoding mCherry-FGF2 and EGFP-ASC fusion proteins.

In order to clone pmCherry-C3-FGF2 (18 kDa isoform) plasmid encoding the mCherry-FGF2 fusion protein, cDNA of 18 kDa isoform of FGF2 gene was amplified from a cDNA library synthesized using RNA isolated from HeLa cells, using primers HindIII_Fgf2_F (ctataagcttatggcagc-cgggagcatcacc) and EcoRI_Fgf2_R (atgaattcagctcttagcaga-cattggaag). The PCR product digested with HindIII and EcoRI enzymes was cloned by ligating into pmCherry-C3.1 vector digested with the same enzymes.

In order to clone pEGFP-C3-ASC plasmid encoding the EGFP-ASC fusion protein, the DNA sequence encoding the human ASC protein was digested out from the pcDNA3-ASC plasmid using HindIII-EcoRI enzymes and EGFP-ASC fusion protein coding sequence was created by ligating this DNA sequence into EGFP-C3 vector's multiple cloning site digested with the same enzymes. pEGFP-C3 vector was purchased from Clontech.

Example 5

Coating of mCherry-ASC specks' outer shell with peptides fused to EGFP via hydrophobic interactions.

If the antigen and/or bioactive molecule is unable to coat the outer shell of the ASC speck carrier as shown in Example 3, then it should be linked to a structure with hydrophobic properties.

For example, when the hydrophilic EGFP protein (EGFP-stop, SEQ ID NO: 2) encoding plasmid was co-transfected with mCherry-ASC encoding plasmid, the EGFP protein (SEQ ID NO: 2) did not co-localize with the ASC speck carrier composed of mCherry-ASC fusion proteins and it did not coat the outer shell of the ASC speck carrier (FIG. 3A-C).

However, when a fusion protein was created with EGFP protein (SEQ ID NO: 2) and the hydrophobic Peptide 1 (SEQ ID NO: 4) and the plasmid encoding this fusion protein was co-transfected with the mCherry-ASC encoding plasmid, EGFP-Peptide 1 coated the outer shell of the ASC speck carrier composed of mCherry-ASC fusion proteins (FIG. 3D-F).

When a fusion protein was created from EGFP protein (SEQ ID NO: 2) and hydrophilic Peptide 2 (SEQ ID NO: 8) or Peptide 3 (SEQ ID NO: 9), these fusion proteins did not coat the outer shell of the mCherry-ASC specks (FIG. 3G-L). Peptide 1 (SEQ ID NO: 4), Peptide 2 (SEQ ID NO: 8) and Peptide 3 (SEQ ID NO: 9) are 26 amino acids long.

It was tested whether shorter versions of the hydrophobic Peptide 1 (SEQ ID NO: 4) could also coat the outer shell of the ASC speck via their hydrophobic properties and form the inventive composition together with ASC specks. These shortened peptide sequences are 19, 12 and 8 amino acids long versions of Peptide 1. Among these shortened peptides, only EGFP-Peptide 1_19aa fusion protein coated the outer shell of mCherry-ASC specks, when 19 amino acids long Peptide 1_19aa (SEQ ID NO: 5) was in a fusion protein with EGFP protein (SEQ ID NO: 2) (FIG. 4A-C). When fusion proteins were created with even shorter versions of Peptide 1, being Peptide 1_12aa (SEQ ID NO: 6) or Peptide 1_8aa (SEQ ID NO: 7), and EGFP (SEQ ID NO: 2); these fusion proteins did not coat the outer shell of mCherry-ASC specks (FIG. 4D-I). Thus, the shortest length of a hydrophobic peptide required to load a protein to ASC specks should be at least 13 amino acids long.

Hydropathy graphs of peptides mentioned above were given (FIG. 5). According to hydropathy graphs and calculated mean hydrophobicity values (Table 1), it appears that Peptide 1 (SEQ ID NO: 4) and its shorter versions are more hydrophobic compared to Peptide 2 (SEQ ID NO: 8) and Peptide 3 (SEQ ID NO: 9). No relationship between electrical charges of peptides given in Table 1 and their ability to be loaded to mCherry-ASC specks could be found. It has been previously shown that the ASC protein (SEQ ID NO: 1) surface is rich in evolutionarily conserved hydrophobic amino acids and these amino acids are critical for ASC protein (SEQ ID NO: 1) oligomerization (Moriya et al. 2005). Taken together, it has been shown that the reason for the capability of EGFP-Peptide 1 and EGFP-Peptide 1_19aa fusion proteins to be loaded to mCherry-ASC specks is their hydrophobic structure.

TABLE 1

Properties of peptides fused to EGFP.

| | Length | Mean hydrophobicity | Charge (pH = 7) | Ability to be loaded to specks |
|---|---|---|---|---|
| Peptide 1 (SEQ ID NO: 4) | 26 | 1.98 | 0 | + |
| Peptide 2 (SEQ ID NO: 8) | 26 | −1.96 | −1.9 | − |
| Peptide 3 (SEQ ID NO: 9) | 26 | −1.4 | −3 | − |
| Peptide 1_19aa (SEQ ID NO: 5) | 19 | 3.22 | −1 | + |
| Peptide 1_12aa (SEQ ID NO: 6) | 12 | 2.39 | −1 | − |
| Peptide 1_8aa (SEQ ID NO: 7) | 8 | 2.89 | −1 | − |

Hydropathy graphs (FIG. 5) and calculated electrical charges of peptides at pH=7.0 in Table 1 were calculated using the application at http://www.innovagen.se/custom-peptide-synthesis/peptide-property-calculator/peptide-property-calculator.asp. Mean hydrophobicity values of peptides given in Table 1 were calculated using the application at http://www.bbcm.univ.trieste.it/~tossi/HydroCalc/HydroMCalc.html.

Co-transfection of mCherry-ASC and EGFP-Peptide X (X is Peptide 1 (SEQ ID NO: 4), Peptide 1_19aa (SEQ ID NO: 5), Peptide 1_12aa (SEQ ID NO: 6), Peptide 1_8aa (SEQ ID NO: 7), Peptide 2 (SEQ ID NO: 8), Peptide 3 (SEQ ID NO: 9) encoding plasmids and purification of specks from cell culture were carried out as described in Example 3.

Cloning of EGFP-X plasmids was carried out as follows: pEGFP-Peptide 1, pEGFP-Peptide 2, pEGFP-Peptide 3.

The 22 amino acids long section of the 26 amino acids long sequence encoded by the multiple cloning site of pEGFP-C3 vector was switched with 3 randomly chosen peptides of the same length. These peptides are three consecutive sequences selected from the ampicillin resistance gene of pcDNA3 vector. Peptide (SEQ ID NO: 4) was amplified in PCR with BglII_Amp1_F (ataagatcttatgagtat-tcaacatttccgtgtc) and EcoRI_Amp1_R (tgaattcaaaaaacag-gaaggcaaaatgcc) primers, Peptide 2 (SEQ ID NO: 8) with BglII_Amp2_F (tctagatcttgctcacccagaaacgctggtg) and EcoRI_Amp2_R (tgaattcagtaacccactcgtgcacccaac) primers, Peptide 3 (SEQ ID NO: 9) with BglII_Amp3_F (ataagatct-tatcgaactggatctcaacagcg) and EcoRI_Amp3_R (tgaattcacat-tggaaaacgttcttcgg) primers and cloned between the BglII-EcoRI sites in pEGFP-C3 vector by digesting the PCR product and the vector with these enzymes and ligating to each other.

Shorter Versions of pEGFP-Peptide 1.

15, 8 and 4 amino acids long versions of Peptide 1 cloned from ampicillin resistance gene were subcloned by ligation of ordered oligonucleotides to BglII-EcoRI sites in pEGFP- C3 vector (15, 8 and 4 amino acids long peptides form 19, 12, 8 amino acids long peptides with YSDL sequence at their beginning) In order to clone pEGFP-Peptide 1_19aa (SEQ ID NO: 5), amp1_19aa_F (gatcttgtcgcccttattccctttttgcggcattttgccttcctgtttttg) and amp1_19aa_R (aattcaaaaaacaggaaggcaaaatgccgcaaaaaagggaataagggcgacaa) oligonucleotides; to clone pEGFP-Peptide 1_12aa (SEQ ID NO: 6), amp1_12aa_F (gatcttgcggcattttgccttcctgtttttg) and amp1_12aa_R (aattcaaaaaacaggaaggcaaaatgccgcaa) oligonucleotides; and to clone pEGFP-Peptide 1_8aa (SEQ ID NO: 7), amp1_8aa_F (gatcttcttcctgtttttg) and amp1_8aa_R (aattcaaaaaacaggaagaa) oligonucleotides were denatured at 95° C. for 5 minutes and cooled down to room temperature slowly in one hour. The oligonucleotides, self-annealed at their complementary sequences in this way, were cloned between BglII and EcoRI sites in pEGFP-C3 vector by digesting the self-annealed oligonucleotides and the vector with these enzymes and ligating them to each other.

A fusion protein can be created by cloning the preferred antigen/bioactive molecule coding sequence to the N- or C-terminal of Peptide 1, Peptide 1_19aa or any other peptide coding sequence, which achieves loading of antigen/bioactive molecules to ASC specks.

Example 6

Stimulation of EGFP-ASC expressing stable THP-1 cells with proinflammatory stimuli.

The inventive composition comprising ASC specks loaded with antigens and/or bioactive molecules can be synthesized by expressing antigens and/or bioactive molecules fused to the ASC protein in a cell line inducible by proinflammatory stimuli and subsequently stimulating the cells with such proinflammatory stimuli.

Such proinflammatory stimuli can be any stimuli triggering the NLRP3, NLRC4 or AIM2 inflammasomes. The NLRP3 inflammasome can be triggered by monosodium urea (MSU), uric acid, asbestos, silica, aluminium hydroxide, ATP, plasma membrane damaging substances such as nigericin, UVB, hyaluronan, amyloid-β fibers and calcium pyrophosphate dehydrate crystals; the NLRC4 inflammasome can be triggered by flagellin; and the AIM2 inflammasome can be triggered by cytosolic DNA or DNA analogs (polyA:T) (Franchi et al., 2009, Jin et al., 2010).

To create an EGFP-ASC expressing stable cell line, the lentiviral transduction method was employed on THP-1 cells. To produce lentiviruses, the lentiviral plasmid pLenti-Ef1a-EGFP-ASC, encoding the EGFP-ASC fusion protein, was co-transfected with helper plasmids (pCMVdeltaR8.74 and pMD2.G) into HEK 293 FT cells (4 μg of each 3 plasmids were transfected to 5 million cells plated on 100 mm dish). 2 days after transfection, cell culture supernatant containing lentiviruses was passed through a 0.45 μm filter and mixed with polybrene (final concentration: 4 μg/ml). Subsequently, the supernatant containing lentiviruses was added onto THP-1 cell and incubated for 5 hours. The cell culture supernatant was changed after incubation and an increase in the number of cells expressing the EGFP-ASC fusion protein was observed in a period of 5 days. At the end of the 5th day, the cells were plated on 96-well plates so that each well received a single cell, and a stable cell line colony derived from a single cell has been established.

The EGFP-ASC fusion protein expressing stable THP-1 monocyte cell line was differentiated to acquire macrophage characteristics by incubation with 0.5 μM PMA for 3 hours. Differentiated cells were stimulated with 150 μg/ml MSU for 8 hours to activate the NLRP3 inflammasome and it was observed that the cells synthesized EGFP-ASC specks. The rest of the ASC speck purification from cell culture process was carried out as described in Example 1.

For the lentiviral transduction of EGFP-ASC fusion protein into the THP-1 monocyte cell line, the DNA sequence encoding EGFP-ASC was digested out from pEGFP-C3-ASC plasmid with NheI-NotI enzymes and cloned by ligating into pLenti-Ef1a vector digested with the same enzymes. pLenti-Ef1a vector backbone was taken from the pLenti-EF1a-hChR2(H134R)-EYFP-WPRE plasmid. The pLenti-EF1a-hChR2(H134R)-EYFP-WPRE plasmid and the helper plasmids pCMVdeltaR8.74 and pMD2.G were gifts from Deisseroth Lab (Stanford University, Stanford, USA).

In EGFP-ASC expressing stable THP-1 cells, EGFP-ASC fusion proteins were present in the cytosol in a diffused pattern in the absence of proinflammatory stimuli (such as MSU). EGFP-ASC specks were synthesized when cells were stimulated with 150 μg/ml MSU for 8 hours.

A fusion protein can be created by cloning the preferred antigen/bioactive molecule coding sequence to the ASC protein (SEQ ID NO: 1) coding sequence at the N-terminus as in EGFP-ASC example or alternatively at the C-terminus or inside the protein coding sequence.

Example 7

Synthesis of the inventive composition in vitro.

An antigen or a bioactive molecule can be produced as a fusion protein with the ASC protein in a bacterial expression system. Alternatively, the antigen/bioactive molecule and ASC proteins can be produced in a bacterial gene expression system separately (not as a fusion protein). Afterwards, the purified fusion proteins or separately expressed proteins form the inventive composition by incubation at 37° C. in a solution containing <50 mM KCl in vitro.

As an example, 6× histidine-EGFP-ASC fusion protein coding sequence was cloned into pETM-20 vector backbone and the plasmid was transformed into Rosetta2 pLysS bacterial strain. The pET system-controlled gene expression was induced by 0.4 mM IPTG at 15° C. overnight. The bacterial strain was grown in Terrific Broth (12 g tryptone, 24 g yeast extract, 4 ml glycerol, 0.017 M KH2PO4, 0.072M K2HPO4 in 1 L water). Protein purification was performed as described in prior art (Alba, 2007). The bacterial pellet was centrifuged at 8000 rpm for 15 minutes and resuspended in 20 mM Tris pH=8, 500 mM NaCl, 5 mM imidazole and 5 M guanidium hydrochloride containing solution and sonicated. Cell debris was centrifuged at 13000 rpm for 45 minutes and the supernatant was passed through a His-purification column (Pierce). The column was washed in a solution containing 20 mM imidazole and protein was eluted in a solution containing 200 mM imidazole. The elution pH was dropped to pH=4 and dialyzed against water at pH=4.

In vitro speck synthesis was carried out as described in prior art (Fernandes-Alnemri et al., 2007). Purified and dialyzed 10 ng/μl EGFP-ASC protein was incubated at 37° C. for 1 hour in 30 mM Tris-HCl pH 7.5 containing solution.

In order to clone pETM20-6×-His-EGFP-ASC plasmid, the DNA sequence encoding EGFP-ASC fusion protein was digested out from pEGFP-C3-ASC plasmid with NcoI-NotI enzymes and cloned by ligating this sequence into the 6× His containing pETM20 vector digested with the same enzymes.

A fusion protein can be created by cloning the preferred antigen/bioactive molecule coding sequence to ASC protein (SEQ ID NO: 1) coding sequence at the N-terminus as in 6×

Histidine-EGFP-ASC example or alternatively at the C-terminus or inside the protein coding sequence.

Example 8

When the ASC protein (SEQ ID NO: 1) fused to antigen/bioactive molecules is expressed in bacteria, fusion proteins are trapped in inclusion bodies. By using the method described in this example, microparticulate aggregates of ASC proteins derived from inclusion bodies or in vitro ASC specks can be synthesized.

6× histidine-EGFP-ASC fusion protein was cloned into pETM-20 vector backbone and the plasmid was transformed into the Rosetta2 pLysS bacterial strain. The pET system-controlled gene expression was induced with 0.4 mM IPTG at 15° C. overnight. The bacterial strain was grown in Terrific Broth (12 g tryptone, 24 g yeast extract, 4 ml glycerol, 0.017 M KH2PO4, 0.072M K2HPO4 in 1 L water). 30 ml of bacteria were pelleted at 8000 rpm for 15 minutes. Bacterial pellet was resuspended in 10 ml Triton X-100 solution (1% Triton X-100, 150 mM NaCl, 2 mM EDTA, 20 mM Tris-HCl pH=7.5) and incubated at 30° C. for 15 minutes. During the incubation, T7 lysozyme enzyme, present in the Rosetta2 pLysS strain, digested the bacterial cell walls. Subsequently, the bacterial pellet was sonicated and centrifuged at 14000 rpm for 15 minutes. The supernatant phase was enriched in soluble bacterial proteins and this phase was discarded. Next, the pellet was resuspended in PBS solution containing 1% SDS and centrifuged at 14000 rpm for 15 minutes. This time, the supernatant was enriched in 6×-histidine-EGFP-ASC fusion proteins extracted from inclusion bodies. Proteins were precipitated by mixing 1 volume of supernatant with 4 volumes of acetone while SDS remains in the supernatant thanks to the acetone. The mixture was centrifuged at 14000 rpm for 1 minute and the supernatant was discarded. The protein pellet was washed with 4 volumes of acetone for 2 additional times. 1 volume of PBS was added on the pellet and sonicated. We call this method of in vitro speck synthesis from ASC fusion proteins extracted from inclusion bodies the Triton X-100/SDS/Acetone (TSA) method.

When a preparation synthesized from 6× histidine-EGFP-ASC fusion protein using the TSA method was examined under confocal microscopy, micron-sized speck structures were observed.

A fusion protein can be created by cloning the preferred antigen/bioactive molecule coding sequence to ASC protein (SEQ ID NO: 1) coding sequence at N-terminus as in 6× Histidine-EGFP-ASC example or alternatively at C-terminus or inside the protein coding sequence.

Example 9

Obtaining the ASC speck carrier using different ASC homologues.

A fusion protein is created with an antigen/bioactive molecule and the zebrafish homologue of the ASC protein (SEQ ID NO: 11). As an example, the plasmid encoding EGFP-zASC fusion protein was transfected into HEK 293 FT cells, as described in Example 1. The transfection and purification of ASC specks from cell culture were carried out as described in Example 1.

In order to clone the plasmid encoding the EGFP-zASC fusion protein, the zebrafish homologue of ASC protein (zASC) coding sequence was amplified from cDNA synthesized from RNA of 9 days old zebrafish embryos using primers SacI_zAsc_F (atagagctcatggcggaatctttcaaggag; SEQ ID NO:12) and EcoRI_zAsc_R (agaattctactgagcatcctcaaggtc; SEQ ID NO:13) and cloned by digesting PCR product and pEGFP-C3 plasmid with SacI-EcoRI enzymes and ligating to each other. Zebrafish cDNA was a gift from Xalid Bayramli (Bogazici University, Istanbul, Turkey).

A fusion protein can be created by cloning the preferred antigen/bioactive molecule coding sequence to zASC protein (SEQ ID NO: 11) coding sequence at the N-terminus as in EGFP-zASC example or alternatively at the C-terminus or inside the protein coding sequence.

Example 10

Obtaining the inventive composition consisting of an antigen/bioactive molecule and the ASC speck carrier composed of zASC protein.

As an example of loading an antigen/bioactive molecule to the speck carrier formed by the zebrafish ASC protein (SEQ ID NO: 11) via hydrophobic interactions, EGFP-zASC fusion protein and mCherry-Peptide 1 (Peptide 1, SEQ ID NO: 4) fusion protein encoding plasmids were co-transfected into HEK 293 FT cells. Co-transfection and purification of ASC specks from cell culture were carried out as in Example 3. As a result of co-transfection, it was seen that mCherry-Peptide 1 coated the outer shell of the EGFP-zASC specks.

In order to clone pmCherry-C3.1-Peptide 1 plasmid encoding mCherry-Peptide 1 fusion protein, peptid1_XhoI_F (tcgagtactcagatcttatgagtattcaacatttccgtgtcgcccttattcccttttttgcggcattttgccttcctgttttttg; SEQ ID NO:14) and peptid1_EcoRI_R (aattcaaaaaacaggaaggcaaaatgccgcaaaaaagggaataagggcgacacggaaatgttgaatactcataagatctgagtac; SEQ ID NO:15) oligonucleotides were denatured at 95° C. for 5 minutes and cooled down to room temperature slowly in one hour. The oligonucleotides, self-annealed at their complementary sequences in this way, were cloned between XhoI and EcoRI sites in the pmCherry-C3.1 vector by digesting the self-annealed oligonucleotides and the vector with these enzymes and ligating them to each other.

Example 11

The membrane enclosed state of THP-1 cell-engulfed inventive composition inside the cell and its slow degradation.

mCherry-ASC specks were produced by overexpression of the mCherry-ASC fusion proteins in HEK 293 FT cells as described in Example 1. As a result of purification of cell culture-synthesized mCherry-ASC specks as described in Example 1, specks with 2-8 micrometer diameter were obtained. EGFP-ASC protein expressing stable THP-1 cells with macrophage characteristics after treatment with phorbol 12-myristate 13-acetate (PMA) were incubated with the mCherry-ASC specks. Following the 2 hours of incubation, it was observed that mCherry-ASC specks were engulfed by the THP-1 cells containing EGFP-ASC in their cytoplasm in a diffuse distribution and at low concentrations (FIG. 6, t=0 s). In cells analyzed under confocal microscopy, it was observed that signals coming from the stably expressed EGFP-ASC and the newly engulfed mCherry-ASC speck did not overlap. It is known that in EGFP-ASC and mCherry-ASC proteins overexpressing cells, these two fusion proteins are co-localized in the same specks. The lack of co-localization in mCherry-ASC speck endocytosed and stably EGFP-ASC protein expressing THP-1 cells showed that the mCherry-ASC speck was present in a membrane enclosed organelle. This membrane enclosed organelle is the phagolysosome.

Another evidence showing the membrane enclosed state of the engulfed mCherry-ASC specks was obtained during prolonged incubation of THP-1 cells under conditions promoting apoptosis. Under physiological conditions, the endocytosed speck was enclosed with a tight membrane and it was not possible to distinguish the membrane under these conditions. However, during prolonged incubation of PMA differentiated THP-1 cells in an unphysiological environment, the plasma membrane integrity of cells was lost (membrane blebbing). In order to promote the gradual progression of cells into apoptosis, THP-1 cells were kept between a slide and a coverslip in PBS and imaged >30 minutes.

Simultaneously with plasma membrane deformation, the phagolysosome membrane was deformed and expanded. Thus, the membrane enclosing the engulfed ASC speck in the phagolysosome became visible. Besides, it was clearly observed that the space inside the phagolysosome but outside of the spherical speck structure was filled with mCherry-ASC, which has detached from the ASC speck (FIG. 6, t=600 s to t=1100 s). The mCherry-ASC speck carrier was distinguishable under bright field microscopy image as a solid, spherical structure inside the phagolysosome. The great majority of the mCherry-ASC signal coming from the phagolysosome organelle came from this structure. In FIG. 6, in order to show the mCherry-ASC signal in the space inside the phagolysosome but outside of the spherical speck structure, the signal in the spherical speck structure was saturated and so the differences between the two regions were not clear. Nevertheless, the intensity of the signal coming from the mCherry-ASC speck carrier was far greater than the diffuse mCherry-ASC signal in the phagolysosome, indicating a slow and controlled degradation inside the phagolysosome. Besides, the lack of complete mCherry-ASC speck degradation in the time period cells were observed under confocal microscopy and the stability of the mCherry-ASC specks at 37° C. for at least 30 days in solution, suggested that the controlled degradation in the phagolysosome may take a period of hours or even days.

The THP-1 cells underwent apoptosis not because of the engulfed ASC specks but because of prolonged exposure to unphysiological conditions. THP-1 cells, incubated with mCherry-ASC specks for different periods of time, preserved their membrane integrity in the first 5-10 minutes of imaging, while cell death was observed around the 20th minute. Moreover, cells could preserve their membrane integrity, when they were examined using a growth chamber for the same amount of time.

Example 12

Tubular Vesicles' pinching-off from phagolysosomes containing the inventive composition.

When EGFP-ASC expressing stable THP-1 cells having engulfed mCherry-ASC specks were time-lapse imaged under confocal microscopy using growth chambers maintaining cell culture conditions, it was observed that mCherry-ASC specks preserved their spherical structure inside the cell, while mCherry-ASC containing tubular vesicles were pinching-off from the phagolysosome (FIG. 7). The time required for the total degradation of engulfed specks is unknown. Nevertheless, this finding suggests that antigens carried with the ASC speck carrier can be degraded in the phagolysosome in a controlled manner and they can enter into the antigen presentation pathway by leaving the phagolysosome organelle in tubular vesicles. In order to enter the antigen presentation pathway, this type of vesicles should fuse with MHC class II molecule containing vesicles and reach the plasma membrane.

Moreover, mCherry-ASC containing vesicles pinching-off from the phagolysosome did not overlap with the cytoplasmic EGFP-ASC. This is also an evidence for the hypothesis that the structures pinching-off from the phagolysosome are membrane enclosed vesicles.

In order to keep the THP-1 macrophage cells viable during time-lapse imaging, a homemade growth chamber was employed. Agarose gel was poured on a 60 mm plate and a piece with the size of a coverslip was cut and removed from the agarose gel. The agarose gel was warmed to 37° C. and the gap in the gel was filled with cell culture medium at 37° C. A THP-1 cell-plated coverslip was mounted on the growth chamber upside down and imaging was done under confocal microscopy. In this way, it was observed that THP-1 cell membranes remain stable for at least 30 minutes.

Example 13

Endurance of the inventive composition against prolonged incubation at 37° C.

In order to measure the stability of the composition at physiological temperature (37° C.) in vitro, which was composed of antigen or bioactive molecule loaded to ASC speck carrier as a fusion protein or via hydrophobic interactions, mCherry-ASC encoding plasmid was transfected into HEK 293 FT cell alone or with EGFP-Peptide 1 encoding plasmid (Peptide 1, SEQ ID NO: 4).

The ASC specks were isolated from cell culture as described in Example 1 and incubated in PBS solution at 37° C. for 30 days. At the end of 30th day, it was observed that spherical structures of mCherry-ASC specks and spherical shell structures composed of EGFP-Peptide 1 coating the outer shell of mCherry-ASC specks were maintained (FIG. 8).

Example 14

Endurance of the inventive composition against freeze-thaw cycles.

The inventive compositions synthesized and purified as in Example 1 and Example 4 were subjected to 8 consecutive freeze-thaw cycles (from −80° C. to +37° C.). Freeze-thawed compositions in a unit area were imaged under confocal microscopy and counted. No statistically significant differences could be detected between the first and the last freeze-thaw cycles. As an example, the fused-composition composed of mCherry-ASC specks was shown (FIG. 9).

References cited in the description are given below.

REFERENCES

Balmayor E R, Azevedo H S, Reis R L. (2011) Controlled delivery systems from pharmaceuticals to cells and genes. Pharm Res. 28(6):1241-58.

De Alba E (2007) 1H, 15N and 13C backbone and side chain chemical shifts of human ASC (apoptosis-associated speck-like protein containing a CARD domain). Biomol NMR Assign. 1(1):135-7

De Temmerman M L, Rejman J, Demeester J, Irvine D J, Gander B, De Smedt S C. (2011) Particulate vaccines on the quest for optimal delivery and immune response. Drug Discov Today. 16(13-14):569-82.

Ellebedy A H, Lupfer C, Ghoneim H E, DeBeauchamp J, Kanneganti T D, Webby R J. (2011) Inflammasome-independent role of the apoptosis-associated speck-like protein containing CARD (ASC) in the adjuvant effect of MF59. Proc Natl Acad Sci USA. 108(7):2927-32.

Fernandes-Alnemri T, Wu J, Yu J W, Datta P, Miller B, Jankowski W, Rosenberg S, Zhang J, Alnemri E S. (2007) The pyroptosome: a supramolecular assembly of ASC dimers mediating inflammatory cell death via caspase-1 activation. Cell Death Differ. 14(9):1590-604.

Franchi L, Eigenbrod T, Muñoz-Planillo R, Nuñez G. (2009) The inflammasome: a caspase-1-activation platform that regulates immune responses and disease pathogenesis. Nat Immunol. 10(3):241-7.

Gross O, Thomas C J, Guarda G, Tschopp J. (2011) The inflammasome: an integrated view Immunol Rev. 243(1): 136-51.

Jin C, Flavell R A. (2010) Molecular mechanism of NLRP3 inflammasome activation. J Clin Immunol. 30(5):628-31.

Leemans J C, Cassel S L, Sutterwala F S. (2011) Sensing damage by the NLRP3 inflammasome Immunol Rev. 243(1):152-62.

Masumoto J, Zhou W, Chen F F, Su F, Kuwada J Y, Hidaka E, Katsuyama T, Sagara J, Taniguchi S, Ngo-Hazelett P, Postlethwait J H, Núñez G, Inohara N. (2003) Caspy, a Zebrafish Caspase, Activated by ASC Oligomerization Is Required for Pharyngeal Arch Development J Biol Chem. 7; 278(6):4268-76.

Miao E A, Rajan J V, Aderem A. (2011) Caspase-1-induced pyroptotic cell death. Immunol Rev. 243(1):206-14.

Moriya M, Taniguchi S, Wu P, Liepinsh E, Otting G, Sagara J. (2005) Role of Charged and Hydrophobic Residues in the Oligomerization of the PYRIN Domain of ASC Biochemistry. 18; 44(2):575-83.

Xiang S D, Scholzen A, Minigo G, David C, Apostolopoulos V, Mottram P L, Plebanski M. (2006) Pathogen recognition and development of particulate vaccines: Does size matter? Methods. 40(1):1-9.

The invention claimed is:

1. A composition that functions in the delivery of antigens and/or bioactive molecules to antigen presenting cells, comprising at least one apoptosis-associated speck-like protein containing a CARD (ASC) speck carrier comprising ASC proteins; and at least one peptide/protein, being an antigen of a pathogen and/or a therapeutic bioactive molecule, carried by the ASC speck carrier.

2. A composition according to claim 1, wherein (i) the antigen of a pathogen is at least one member of the group consisting of peptides, proteins and peptides mimicking carbohydrates or a mixture of at least two members of these groups that can stimulate antibody production upon entering into the body, or (ii) the therapeutic bioactive molecule is at least one member of the group consisting of drugs, growth factors, hormones, receptors, receptor ligands, adjuvants and antibodies or a mixture of at least two members of these groups.

3. A composition according to claim 1, wherein the ASC speck carrier carries at least one type of antigen of a pathogen and/or at least one type of therapeutic bioactive molecule.

4. A composition according to claim 1, wherein (i) the ASC speck carrier releases the peptide/protein, being the antigen of a pathogen and/or the therapeutic bioactive molecule, in an acidic environment, (ii) the ASC speck carrier being biodegradable by hydrolysis or enzymes, and/or (iii) the antigen of a pathogen and/or the therapeutic bioactive molecule exists as a fusion protein with at least one ASC protein forming the ASC speck carrier and is carried by the ASC speck carrier as a fusion protein.

5. A composition according to claim 4, wherein the antigen and/or the bioactive molecule is comprised within a fusion protein with the ASC protein and is fused to the ASC protein at the N-terminus, the C-terminus, or inside the ASC speck carrier.

6. A composition according to claim 5, wherein the antigen of a pathogen and/or the therapeutic bioactive molecule is carried inside the ASC speck carrier.

7. A composition according to claim 1, wherein the antigen of a pathogen and/or the therapeutic bioactive molecule is carried by the ASC speck carrier by forming hydrophobic interactions with the ASC proteins forming the ASC speck carrier.

8. A composition according to claim 7, wherein the antigen of a pathogen and/or the therapeutic bioactive molecule comprises at least one type of peptide/protein being at least 13 amino acids long.

9. A composition according to claim 8, wherein the antigen of a pathogen and/or the therapeutic bioactive molecule comprises at least one type of peptide/protein being hydrophobic.

10. A composition according to claim 9, wherein the antigen of a pathogen and/or the therapeutic bioactive molecule is carried by coating the outer shell of the ASC speck carrier.

11. A composition according to claim 1, wherein the antigen of the pathogen and/or the therapeutic bioactive molecule comprises at least one type of peptide/protein.

12. A composition according to claim 1, comprising at least one apoptosis-associated speck-like protein containing a CARD (ASC) speck carrier comprising ASC proteins, and at least one peptide/protein that is an antigen of a pathogen, and is carried by the ASC speck carrier.

13. A composition according to claim 1, comprising at least one apoptosis-associated speck-like protein containing a CARD (ASC) speck carrier comprising ASC proteins, and at least one peptide/protein that is a therapeutic bioactive molecule, and is carried by the ASC speck carrier, wherein the therapeutic bioactive molecule is at least one member of the group consisting of growth factors, hormones, receptors, receptor ligands, adjuvants and antibodies or a mixture of at least two members of these groups.

14. A composition that functions in the delivery of vaccine antigens and/or bioactive molecules to antigen presenting cells, comprising at least one apoptosis-associated speck-like protein containing a CARD (ASC) speck carrier comprising ASC proteins; and at least one peptide/protein, being a vaccine antigen and/or a therapeutic bioactive molecule, carried by the ASC speck carrier.

15. A method for producing the composition according to claim 1, the method comprising the steps of:

forming at least one ASC speck carrier by ASC proteins coming together;

loading at least one peptide/protein, being the antigen of a pathogen and/or the therapeutic bioactive molecule, to the ASC speck carrier; and obtaining the composition comprising ASC speck carrier and at least one peptide/protein, being the antigen of a pathogen and/or the therapeutic bioactive molecule, loaded to the ASC speck carrier.

16. A method according to claim 15, wherein the peptide/protein, being the antigen of a pathogen and/or the therapeutic bioactive molecule, is loaded to ASC proteins forming ASC speck carrier as a fusion protein, in the step of loading at least one peptide/protein, being the antigen of a pathogen and/or the therapeutic bioactive molecule, to the ASC speck carrier, and/or the composition comprising the ASC speck carrier and at least one peptide/protein, being the antigen of a pathogen and/or the therapeutic bioactive molecule, is synthesized in cell culture and purified from cell culture, in the step of obtaining the composition.

17. A method according to claim 16, wherein the composition is synthesized in cell culture by the stimulation of cells with proinflammatory stimuli and/or the composition is synthesized in cell culture without a stimulus via overexpression of plasmids containing at least one DNA sequence encoding the ASC protein in cell culture.

18. A method according to claim 15, wherein (i) the composition is synthesized using purified fusion proteins comprising the ASC protein forming the ASC speck carrier and the peptide/protein, being the antigen of a pathogen and/or the therapeutic bioactive molecule, in the step of obtaining the composition, and optionally (ii) the composition is synthesized in vitro by incubating the fusion proteins comprising the ASC protein forming the ASC speck carrier and the peptide/protein, being the antigen of a pathogen and/or the therapeutic bioactive molecule, in a hypotonic solution at 37° C., in the step of obtaining the composition.

19. A production method for a composition according to claim 15, wherein (i) the peptide/protein, being the antigen of a pathogen and/or the therapeutic bioactive molecule, is loaded to the ASC speck carrier via hydrophobic interactions with the ASC speck carrier, in the step of loading at least one peptide/protein, being the antigen of a pathogen and/or the therapeutic bioactive molecule, to the ASC speck carrier, and optionally (ii) the peptide/protein sequence, being the antigen of a pathogen and/or the therapeutic bioactive molecule, loaded to the ASC speck carrier via hydrophobic interactions, comprises at least one type of peptide/protein being at least 13 amino acids long and hydrophobic, in the step of loading at least one peptide/protein, being the antigen of a pathogen and/or the therapeutic bioactive molecule, to the ASC speck carrier.

20. A method according to claim 19, wherein the composition, comprising the ASC speck carrier and at least one peptide/protein, being the antigen of a pathogen and/or the therapeutic bioactive molecule, loaded to the ASC speck carrier via hydrophobic interactions, is synthesized in cell culture and purified from cell culture, in the step of obtaining the composition.

21. A method according to claim 20, wherein the composition is synthesized in cell culture by the stimulation of cells with proinflammatory stimuli and/or the composition is synthesized in cell culture without a stimulus via overexpression of plasmids containing at least one DNA sequence encoding the ASC protein in cell culture.

22. A method according to claim 19, wherein the composition is synthesized using purified ASC proteins forming the ASC speck carrier and purified peptide/protein, being the antigen of a pathogen and/or the therapeutic bioactive molecule, in the step of obtaining the composition, and optionally the composition is synthesized in vitro by mixing the ASC proteins forming the ASC speck carrier and the peptide/protein, being the antigen of a pathogen and/or the therapeutic bioactive molecule, in a hypotonic solution at 37° C. incubation, in the step of obtaining the composition.

23. A method of delivering an antigen of a pathogen or a therapeutic bioactive molecule to a subject, the method comprising administering to the subject a composition of claim 1.

24. A method of inducing an immune response to a pathogen in a subject in need thereof, the method comprising administering to the subject a composition of claim 1, wherein the ASC speck carrier carries at least one peptide/protein that is an antigen of the pathogen.

* * * * *